US012698500B2

(12) United States Patent
Park et al.

(10) Patent No.: US 12,698,500 B2
(45) Date of Patent: Aug. 4, 2026

(54) CTGF GENE-SPECIFIC DOUBLE-STRANDED OLIGONUCLEOTIDE, AND A COMPOSITION FOR PREVENTING AND TREATING FIBROTIC DISEASES AND RESPIRATORY-RELATED DISEASES COMPRISING SAME

(71) Applicant: BIONEER CORPORATION, Daejeon (KR)

(72) Inventors: Han-Oh Park, Sejong-si (KR); Tae-Rim Kim, Daejeon (KR); Young-Ho Ko, Daejeon (KR); Sung Il Yun, Daejeon (KR); Jun Hong Park, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 961 days.

(21) Appl. No.: 17/778,836

(22) PCT Filed: Oct. 29, 2020

(86) PCT No.: PCT/KR2020/014948
§ 371 (c)(1),
(2) Date: May 21, 2022

(87) PCT Pub. No.: WO2021/101113
PCT Pub. Date: May 27, 2021

(65) Prior Publication Data

US 2023/0042493 A1 Feb. 9, 2023

(30) Foreign Application Priority Data

Nov. 22, 2019 (KR) ........................ 10-2019-0151673

(51) Int. Cl.
*C12N 15/113* (2010.01)

(52) U.S. Cl.
CPC ...... *C12N 15/1136* (2013.01); *C12N 2310/14* (2013.01); *C12N 2310/351* (2013.01)

(58) Field of Classification Search
None
See application file for complete search history.

(56) References Cited

U.S. PATENT DOCUMENTS

| | | | |
|---|---|---|---|
| 5,660,985 A | 8/1997 | Pieken et al. | |
| 5,808,023 A | 9/1998 | Sanghvi et al. | |
| 5,958,691 A | 9/1999 | Pieken et al. | |
| 6,175,001 B1 | 1/2001 | Barbas et al. | |
| 6,326,358 B1 | 12/2001 | Manoharan | |
| 6,531,584 B1 | 3/2003 | Cook et al. | |
| 7,622,454 B2 | 11/2009 | Shepard et al. | |
| 9,446,062 B2 | 9/2016 | Feinstein et al. | |
| 9,963,702 B2 | 5/2018 | Khvorova et al. | |
| 2006/0059629 A1 | 3/2006 | Antinori | |
| 2012/0164151 A1 | 6/2012 | Brandan et al. | |
| 2012/0238937 A1* | 9/2012 | Dean | A61P 17/02 604/20 |
| 2013/0178510 A1 | 7/2013 | Sternlicht et al. | |
| 2014/0065162 A1 | 3/2014 | Lipson et al. | |
| 2014/0187610 A1* | 7/2014 | Seeley | C12N 15/113 536/24.5 |
| 2016/0122764 A1* | 5/2016 | Chae | A61P 11/16 536/24.5 |

FOREIGN PATENT DOCUMENTS

| | | |
|---|---|---|
| CN | 103108642 A | 5/2013 |
| CN | 103635197 A | 3/2014 |
| CN | 108251420 A | 7/2018 |
| JP | 2012520683 A | 9/2012 |
| JP | 2014210789 A | 11/2014 |
| JP | 2015518721 A | 7/2015 |
| KR | 10-0883471 B1 | 2/2009 |
| KR | 100883471 B | 2/2009 |
| KR | 101224828 B1 | 1/2013 |
| KR | 1020160033125 A | 3/2016 |
| WO | 2011119887 A1 | 9/2011 |
| WO | 2012005898 A2 | 1/2012 |
| WO | 2015152693 A2 | 10/2015 |

OTHER PUBLICATIONS

English translation of written opinion of the international searching authority for PCT/KR2020/014948, pp. 1-8 (Year: 2021).*
Lam et al. Mol Ther Nucleic Acids 4:e252, pp. 1-20 (Year: 2015).*
Duisters et al. Circulation Research 104:170178 (Year: 2009).*
Yano et al. Radiation and Environmental Biphysics 60:411-419 (Year: 2021).*
Ui-Tei (Nucleic Acid Res. 32:936-948 (Year: 2004).*
Office Action issued in Canadian Patent Application No. 3,158,896 on May 12, 2023.
Office Action issued in Japanese Patent Application No. 2022-529798 on Jun. 19, 2023.
English Translation of Office Action issued in Japanese Patent Application No. 2022-529798 on Jun. 19, 2023.
Habibian, M,et al., "Structural properties and gene-silencing activity of chemically modified DNA-RNA hybrids with parallel orientation", Nucleic Acids Research, 2018, pp. 1614-1623, vol. 46, No. 4.

(Continued)

*Primary Examiner* — Brian Whiteman
(74) *Attorney, Agent, or Firm* — HULTQUIST PLLC; Steven J. Hultquist

(57) ABSTRACT

The present invention relates to a double-stranded oligonucleotide capable of inhibiting CTGF expression with a very specific and high efficiency, a double-stranded oligonucleotide structure and nanoparticles comprising the double-stranded oligonucleotide, and a use thereof in preventing or treating of fibrotic or respiratory diseases.

16 Claims, 5 Drawing Sheets

Specification includes a Sequence Listing.

(56) References Cited

OTHER PUBLICATIONS

Office Action Issued in Japanese Patent Application No. 2022-529798 on Nov. 6, 2023.
English Translation Office Action Issued in Japanese Patent Application No. 2022-529798 on Nov. 6, 2023.
Office Action issued on Nov. 1, 2024 for Chinese Patent Application 202080093194.8.
English Translation of Office Action issued on Nov. 1, 2024 for Chinese Patent Application 202080093194.8.
Muller, S., et al., "Spliceosomal Peptide P140 for Immunotherapy of Systemic Lupus Erythematosus", Arthritis & Rheumatism, 2008, pp. 3873-3883, vol. 58, No. 12.
Negadova, E.V., et al., "The prevalence of respiratory diseases among the children of the garrison, the role staphylococcal infection in the etiology of respiratory diseases", Hospital of the city of Akhtubinsk FGU 1602 OVKG, 2011, Publisher: Ministry of Defense of Russia.
Negadova, E.V., et al., English Translation of "The prevalence of respiratory diseases among the children of the garrison, the role staphylococcal infection in the etiology of respiratory diseases", Hospital of the city of Akhtubinsk FGU 1602 OVKG, 2011, Publisher: Ministry of Defense of Russia.
Office Action issued in counterpart Russian Patent Application No. 2022116336 on Feb. 7, 2023.
English Translation of Office Action issued in counterpart Russian Patent Application No. 2022116336 on Feb. 7, 2023.
Search Report Issued in Russian Patent Application No. 2022116336 on Feb. 7, 2023.
Vasilieva, O.V., et al., "Connective Tissue Growth Factor (CTGF) in the Human Dermis through Ontogenesis", Ontogeny, 2016attached, pp. 75-82, vol. 47, No. 2.
Vasilieva, O.V., et al., English Abstract of "Connective Tissue Growth Factor (CTGF) in the Human Dermis through Ontogenesise", Otogeny, 2016, pp. 75-82, vol. 47, No. 2.
Search Report issued on February, 5, 2024 for the EP Patent Application No. 20890649.5.
Akhtar, S., et al., "Nonviral delivery of synthetic siRNAs in vivo", The Journal of Clinical Investigation, Dec. 2007, pp. 3623-3632, vol. 117, No. 12, Publisher: http://www.jci.org.
Amarzguioui, M., et al., "Tolerance for mutations and chemical modifications in a siRNA", Nucleic Acids Research, 2003, pp. 589-595, vol. 31, No. 2, Publisher: Oxford University Press.
Barik, S., "Silence of the transcripts: RNA interference in medicine", J Mol Med, 2005, pp. 764-773, vol. 83, Publisher: Springer-Verlag 2005.
Barnes, P., et al., "COPD: current therapeutic interventions and future approaches", Eur Respir J, 2005, pp. 1084-1106, vol. 25, Publisher: ERS Journals Ltd.
Behlke, M., "Progress Towards in Vivo Use of siRNAs", Molecular Therapy, Apr. 2006, pp. 644-670, vol. 13, No. 4, Publisher: The American Society of Gene Therapy.
Braasch, D.A., et al., "Biodistribution of phosphodiester and phosphorothioate siRNA", Bioorganic & Medicinal Chemistry Letters, 2004, pp. 1139-1143, vol. 14, Publisher: Elsevier.
Bramsen, J.B., et al., "A screen of chemical modifications identifies position-specific modification by UNA to most potently reduce siRNA off-target effects", Nucleic Acids Research, 2010, pp. 5761-5773, vol. 38, No. 17, Publisher: Oxford University Press.
Brigstock, D.. , "Connective tissue growth factor (CCN2, CTGF) and organ fibrosis: lessons from transgenic animals", J. Cell Commun. Signal., 2010, pp. 1-4, vol. 4, Publisher: Springer.
Castaldi, P., et al., "The COPD genetic association compendium: a comprehensive online database of COPD genetic associations", Human Molecular Genetics, 2010, pp. 526-534, vol. 19, No. 3, Publisher: Oxford University Press.
Chery, J., "RNA therapeutics: RNAi and antisense mechanisms and clinical applications", Journal of Postdoctoral Research, Jul. 2016, pp. 35-50, vol. 4, No. 7, Publisher: www.PostdocJournal.com.
Chiu, Y-L, et al., "siRNA function in RNAi: A chemical modification analysis", RNA, 2003, pp. 1034-1048, vol. 9, Publisher: Cold Spring Harbor Laboratory Press.
Crooke, S., "Progress in Antisense Technology", Annu. Rev. Med., 2004, pp. 61-95, vol. 55, Publisher: Annual Reviews.
Dorsam, R., "Non-clinical Experience with RNA-based Loigonucleotide Therapeutics", U.S. Food and Drug Administration, 2012.
Kim, S., et al., "Local and systemic delivery of VEGF siRNA using polyelectrolyte complex micelles for effective treatment of cancer", Journal of Controlled Release, 2008, pp. 107-116, vol. 129, Publisher: Elsevier.
Kim, H., et al., "Polymer-Based Hybrid Materials for Gene Delivery and Silencing", Polymer Science and Technology, 2012, pp. 254-259, vol. 23, No. 3.
Kim, H., et al., "Polymer-Based Hybrid Materials for Gene Delivery and Silencing", Polymer Science and Technology, 2012, pp. 254-259; Eng Translation, vol. 23, No. 32.
Pauwels, R., et al., "Global Strategy for the Diagnosis, Management, and Prevention of Chronic Obstructive Pulmonary Disease", Am J Respir Crit Care Med, 2001, pp. 1256-1276, vol. 163, Publisher: NHLBI/WHO Workshop Summary.
Remington, J.P., "Remington's Pharmaceutical Sciences", 17th Edition, 1985, pp. 1409-1677, vol. 17th Edition, Publisher: Mack Publishing Company, Easton, PA.
Shigeta, K., et al., "Novel histidine-conjugated galactosylated cationic liposomes for efficient hepatocyte-selective gene transfer in human hepatoma HepG2 cells", Journal of Controlled Release, 2007, pp. 262-270, vol. 118, Publisher: Elsevier.
Soutschek, J., et al., "Therapeutic silencing of an endogenous gene by systemic administration of modified siRNAs", Nature, Nov. 2004, pp. 173-178, vol. 432, Publisher: Nature Publishing Group.
Vaish, N., et al., "Improved specificity of gene silencing by siRNAs containing unlocked nucleobase analogs", Nucleic Acids Research, 2011, pp. 1823-1832, vol. 39, No. 5, Publisher: Oxford University Press.
Veronese, F.M., et al., "PEGylation, successful approach to drug delivery", Drug Discovery Today, Dec. 2005, pp. 1451-1458, vol. 10, No. 21, Publisher: Elsevier.
Xie, F., et al., "Harnessing in vivo siRNA delivery for drug discovery and therapeutic development", Drug Discovery Today, 2006, pp. 67-73, vol. 11, No. 1/2, Publisher: Elsevier.
Brigstock, D.R., "Strategies for blocking the fibrogenic actions of connective tissue growth factor (CCN2): From pharmacological inhibition in vitro to targeted siRNA therapy in vivo", J. Cell Commun. Signal., 2009, pp. 5-18, vol. 3, Publisher: Springer.
Lipson, K.E., et al., "CTGF is a central mediator of tissue remodeling and fibrosis and its inhibition can reverse the process of fibrosis", Fibrogenesis & Tissue Repair, 2012, vol. 5 (Suppl 1), No. S24, Publisher: BioMed Central,. Ltd.

* cited by examiner

Box 2: common seq of all species (human, mouse and monkey)
Boxes 1, 10, and 15: similar KD efficacy compared to Rxi-109

| | $IC_{50}$ Concentration |
|---|---|
| 1 | 137.1 |
| 2 | 87.35 |
| 4 | 219.3 |
| 5 | 141.2 |
| 7 | 580.5 |
| 9 | 327.2 |
| 10 | 30.75 |
| 15 | 116.3 |
| PC_Rxi-109 | 42.97 |

SAM-CTGF IC50 = 30.75 nM Rxi-109 IC50 = 42.97 nM

- *p=0.0437 (relative to the PBS)
- *p=0.0451 (relative to the SAMiRNA-rCTGF (R/R))
- PBS = Phosphate Buffered Saline (Vehicle Control)

CTGF GENE-SPECIFIC DOUBLE-STRANDED OLIGONUCLEOTIDE, AND A COMPOSITION FOR PREVENTING AND TREATING FIBROTIC DISEASES AND RESPIRATORY-RELATED DISEASES COMPRISING SAME

CROSS-REFERENCE TO RELATED APPLICATIONS

This is a U.S. national phase under 35 U.S.C. § 371 of International Patent Application No. PCT/KR2020/014948 filed Oct. 29, 2020, which in turn claims priority under 35 U.S.C. § 119 of Korean Patent Application No. 10-2019-0151673 filed Nov. 22, 2019. The disclosures of all such applications are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "636_SeqListing_ST25.txt" created on May 20, 2022 and is 12,353 bytes in size. The sequence listing contained in this .txt file is part of the specification and is hereby incorporated by reference herein in its entirety.

TECHNICAL FIELD

The present invention relates to a double-stranded oligonucleotide capable of very specifically inhibiting CTGF expression with high efficiency, a double-stranded oligonucleotide construct including the double-stranded oligonucleotide, nanoparticles including the same, and the use thereof for the prevention or treatment of fibrosis or respiratory diseases.

BACKGROUND ART

In 1995, Guo and Kemphues discovered that sense RNA was as effective as antisense RNA in inhibiting gene expression using antisense in *C. elegans*, so research has been conducted to determine the cause thereof. In 1998, Fire et al. first found a phenomenon by which double-stranded RNA (dsRNA) is injected and mRNA corresponding thereto is specifically degraded to thus inhibit gene expression, which is termed RNA interference (RNAi). RNAi, which is a method used to inhibit gene expression, is capable of clearly showing the effect of inhibition of gene expression at a low cost in a simple manner, and thus the range of application thereof is increasing.

Because technology for inhibiting gene expression is able to regulate the expression of specific genes, target genes in cancer, genetic diseases and the like, which are caused by overexpression of specific genes, may be eliminated at the mRNA level, based on which this technology may be used as an important tool for the development of therapeutic agents for disease treatment and verification of targets. Conventionally, in order to inhibit the expression of a target gene, technology for introducing a transgene to the target gene is disclosed, and examples thereof include a method of introducing a transgene in the reverse direction (antisense) of the promoter and a method of introducing a transgene in the forward direction (sense) of the promoter.

RNA therapy targeting RNA is a method that removes the function of the corresponding gene using oligonucleotides for target RNA, and is said to be different from conventional therapies, such as those using antibodies and small molecules, which mainly target proteins. There are two major approaches to targeting RNA: double-stranded-RNA-mediated RNAi and use of an antisense oligonucleotide (ASO). Currently, clinical trials to target RNA are being attempted for various diseases.

An antisense oligonucleotide (hereinafter referred to as 'ASO') is short synthetic DNA designed to bind to a target gene based on Watson-Crick base pairing, and has been used to study gene function and to develop therapeutics capable of treating diseases such as cancer at the molecular level because it is capable of specifically inhibiting the expression of a certain nucleotide sequence of a gene. ASO has an advantage in that it may be easily produced by variously setting the inhibition of gene expression, and there have been studies on the use of the same to inhibit the expression of oncogenic genes and the growth of cancer cells. The process by which ASO inhibits the expression of a specific gene is achieved by eliminating mRNA due to RNase H activity induced by binding to a complementary mRNA sequence or by interfering with the formation and progression of a ribosome complex for protein translation. It has also been reported that ASO binds to genomic DNA to form a triple-helix structure, thereby inhibiting gene transcription. Although ASO has the above potential, in order to use the same in clinical practice, it is necessary to improve resistance to nucleases and to be efficiently delivered into target tissues or cells so as to specifically bind to the nucleotide sequence of a gene of interest. Moreover, the secondary and tertiary structures of gene mRNA are important for specific binding of ASO, and since a region in which less of the secondary structure of mRNA is formed is very advantageous for ASO to access, efforts have been made to effectively achieve gene-specific inhibition in vitro as well as in vivo by systematically analyzing a region in which less of the secondary structure of mRNA is formed before ASO synthesis. This ASO is more stable than siRNA, which is a kind of RNA, and has the advantage of being easily soluble in water and saline. Currently, three ASOs have been approved by the Federal Drug Administration (FDA) (Jessica, C., J. Postdoc Res., 4:35-50, 2016).

Since the discovery of the roles thereof, RNA interference (hereinafter referred to as 'RNAi') has been found to act on sequence-specific mRNA in various types of mammalian cells (Barik, S., J. Mol. Med. (2005) 83: 764-773). When long-chain double-stranded RNA is delivered to cells, the delivered double-stranded RNA is processed into small interfering RNA (hereinafter referred to as 'siRNA') of 21 to 23 base pairs (bp) in length by an endonuclease called a dicer, and siRNA binds to RISC (RNA-induced silencing complex) to thus inhibit the expression of a target gene in a sequence-specific manner through a process in which the guide (antisense) strand recognizes and degrades target mRNA. Gene expression inhibition technology using siRNA is useful in research to identify the function of the target gene in the target cell by inhibiting the expression of the target gene in the target cell and observing changes due thereto. In particular, inhibiting the function of a target gene in an infectious virus or cancer cell will be useful in developing a treatment method for the disease, and it has been reported that siRNA is able to inhibit the expression of target genes based on the results of in-vitro studies and in-vivo studies using experimental animals.

According to Bertrand's research team, it has been found that siRNA for the same target gene has a strong inhibitory effect on the expression of mRNA in vitro and in vivo compared to an antisense oligonucleotide (ASO), and that this effect lasts for a long time. Moreover, since the mechanism of action of siRNA is to regulate the expression of a target gene in a sequence-specific manner by complementary binding to target mRNA, it is advantageous in that the range of targets to which siRNA is applicable is dramatically expanded compared to conventional antibody-based drugs or small molecule drugs (M. A. Behlke, MOLECULAR THERAPY. 2006 13(4):664-670).

Despite the excellent effect of siRNA and the wide range of use thereof, for siRNA to be developed as a therapeutic agent, siRNA must be effectively delivered to target cells by improving in-vivo stability of siRNA and increasing cell delivery efficiency (F. Y. Xie, Drug Discov. Today, 2006 January; 11(1-2):67-73). In order to improve in-vivo stability and solve problems related to nonspecific innate immune stimulation of siRNA, thorough research into modification of some nucleotides or backbones of siRNA so as to be imparted with nuclease resistance, use of a carrier such as a viral vector, liposome or nanoparticles, etc. is ongoing.

A delivery system using a viral vector such as an adenovirus or a retrovirus has high transfection efficacy, but immunogenicity and oncogenicity are high. On the other hand, a non-viral delivery system including nanoparticles has lower cell delivery efficiency than a viral delivery system, but is advantageous because in-vivo stability is high, target-specific delivery is possible, RNAi oligonucleotides are taken up by and internalized into cells or tissues, and there is almost no cytotoxicity or immune stimulation, so the non-viral delivery system is currently considered to be a powerful delivery method compared to the viral delivery system (Akhtar S., J. Clin. Invest. 2007 Dec. 3; 117(12):3623-3632).

Among non-viral delivery systems, the method of use of a nanocarrier includes forming nanoparticles using various polymers such as liposomes, cationic polymer complexes, and the like and loading siRNA on such nanoparticles, namely nanocarriers, to thus deliver the same to cells. Here, specific examples of the nanocarrier may include polymeric nanoparticles, polymer micelles, lipoplexes, and the like. In particular, the lipoplex, which is composed of cationic lipids, interacts with the anionic lipids of the cellular endosome to induce a destabilizing effect of the endosome, thereby realizing intracellular delivery.

In addition, it is known that it is possible to induce high efficiency in vivo by linking a chemical to the end portion of an siRNA passenger (sense) strand to impart enhanced pharmacokinetics (J. Soutschek, Nature 11; 432(7014):173-8, 2004). Here, the stability of siRNA varies depending on the properties of the chemical bound to the end of the siRNA sense (passenger) or antisense (guide) strand. For example, siRNA in a form in which a polymer compound such as polyethylene glycol (PEG) is conjugated interacts with the anionic phosphate group of siRNA in the presence of a cationic material to form a complex, thereby obtaining a delivery carrier having improved siRNA stability (S. H. Kim, J. Control Release 129(2):107-16, 2008). In particular, micelles composed of polymer complexes are extremely small in size compared to other systems used as drug delivery carriers, such as microspheres or nanoparticles, but the distribution thereof is very uniform and occurs spontaneously, resulting in easy formulation quality control and reproducibility.

In order to improve the intracellular delivery efficiency of siRNA, technology has been developed for realizing efficient cell membrane permeability and stability of siRNA using an siRNA conjugate in which a biocompatible polymer hydrophilic material (e.g. polyethylene glycol (PEG)) is conjugated to siRNA through a simple covalent bond or a linker-mediated covalent bond (Korean Patent No. 883471). However, even when siRNA is chemically modified or conjugated to polyethylene glycol (PEG) (PEGylation), it still has disadvantages such as low in-vivo stability and poor delivery to target organs. In order to overcome these disadvantages, a double-stranded oligo RNA construct in which hydrophilic and hydrophobic materials are bound to an oligonucleotide, particularly double-stranded oligo RNA such as siRNA, has been developed, and the construct forms self-assembled nanoparticles called SAMiRNA™ (self-assembled micelle inhibitory RNA) through hydrophobic interaction of the hydrophobic material (Korean Patent No. 1224828). Here, SAMiRNA™ technology is capable of realizing homogenous nanoparticles having a very small size compared to conventional delivery methods.

In a specific embodiment of SAMiRNA™ technology, a hydrophilic material such as PEG (polyethylene glycol) or HEG (hexaethylene glycol) is used. PEG is a synthetic polymer and is often used to increase the solubility of pharmaceuticals, particularly proteins, and to control pharmacokinetics. PEG is a polydisperse material, and a polymer in one batch is composed of a sum of different numbers of monomers, so the molecular weight thereof shows a Gaussian curve, and a polydispersity value (Mw/Mn) represents the extent of homogeneity of a material. Specifically, PEG, having a low molecular weight (3 to 5 kDa), shows a polydispersity value of about 1.01, whereas PEG, having a high molecular weight (20 kDa), shows a high polydispersity value of about 1.2. The higher the molecular weight, the lower the homogeneity of the material. Therefore, when PEG is conjugated to pharmaceuticals, the polydispersity of PEG is reflected in the conjugate, making it difficult to verify a single material, which is undesirable. Hence, a material having a low polydispersity value has to be produced through improvement in PEG synthesis and purification processes. However, in particular, when PEG is bound to a material having a low molecular weight, there are problems related to the polydispersity of the material, such as inconvenience that it is not easy to determine whether binding is easily performed (Francesco M. V. DRUG DISCOVERY TODAY (2005) 10(21):1451-1458).

Accordingly, in recent years, as an improved form of conventional self-assembled nanoparticle SAMiRNA™ technology, blocks in which the hydrophilic material of the double-stranded oligonucleotide construct constituting SAMiRNA™ is blocked into a basic unit including 1 to 15 uniform monomers having a predetermined molecular weight and a linker as necessary are used in an appropriate number depending on the need, whereby a new type of delivery carrier technology with a small size and remarkably improved polydispersity compared to conventional SAMiRNA™ has been developed. It is already known that siRNA is rapidly degraded by various enzymes present in the blood when injected in vivo, thus resulting in poor delivery efficiency to target cells or tissues, and the improved SAMiRNA™ also shows that variation in stability and expression inhibition efficiency is observed depending on the target gene. Therefore, the present inventors have attempted to enhance the expression inhibitory effect and stability of the target gene by applying a double-stranded oligonucleotide in a DNA-RNA hybrid form using a DNA sequence that is an ASO sense strand as a guide and an RNA sequence that is an antisense strand as a passenger, in order to more stably and effectively inhibit the expression of a target gene using improved self-assembled nanoparticles SAMiRNA™.

Chronic obstructive pulmonary disease (hereinafter referred to as 'COPD'), which is a representative lung disease along with asthma, is different from asthma in that it is accompanied by irreversible airway obstruction, and is a respiratory disease that is not completely reversible and progressively restricts airflow, accompanied by an abnormal inflammatory response of the lungs caused by repeated infection, inhalation of harmful particles or gases, or smoking (Pauwels et al., Am J. Respir. Crit. Care Med., 163: 1256-1276, 2001). COPD is a disease caused by pathological changes in the bronchiole and lung parenchyma due to inflammation of the airways and lung parenchyma, and is characterized by bronchiolitis obliterans and emphysema (destruction of the lung parenchyma). Examples of COPD include chronic obstructive bronchitis, chronic bronchiolitis, and emphysema. For COPD, the number of neutrophils increases, and the secretion of cytokines such as GM-CSF, TNF-$\alpha$, IL-8, and MIP-2 is increased. Moreover, the airways become inflamed, the muscle walls thicken, and mucus secretion increases, resulting in bronchial obstruction. When the bronchi are obstructed, the alveoli are enlarged and damaged, oxygen and carbon dioxide exchange capacity is reduced, and the incidence of respiratory failure increases.

The seriousness of COPD has been noted worldwide because COPD was the $6^{th}$ greatest cause of death from disease in 1990, but is predicted to become the $3^{rd}$ greatest cause in 2020, and is the only disease with an increasing incidence among the top 10 diseases. COPD has high prevalence, causes respiratory problems, and incurs high direct medical expenses for diagnosis and treatment of COPD and high indirect medical expenses such as loss due to respiratory distress disorder or leave of absence or loss due to premature death. For this reason, it is becoming a major socioeconomic problem worldwide (Chronic Obstructive Pulmonary Disease (COPD) Medical Guidelines. 2005. Clinical Research Center for Chronic Obstructive Airway Diseases. p. 30-31).

No existing therapies have been confirmed to alleviate the long-term decline in lung function that is characteristic of COPD. Therefore, pharmacotherapy in COPD is mainly used for the purpose of reducing symptoms or complications. In particular, bronchodilators are a representative symptomatic drug for COPD, and anti-inflammatory drugs or corticosteroids are mainly prescribed, but the effectiveness thereof is insignificant, the scope of application is narrow, and there is a high risk of side effects. As for other drugs, only influenza vaccine is known to reduce serious morbidity and mortality in COPD patients by about 50% (Chronic Obstructive Pulmonary Disease (COPD) Medical Guidelines. 2005. Clinical Research Center for Chronic Obstructive Airway Diseases. p. 52-58).

Meanwhile, it is presumed that many genetic factors increase (or decrease) an individual's risk of developing COPD. A genetic risk factor that has been demonstrated to date is genetic deficiency of al-antitrypsin. Although smoking significantly increases the risk of developing COPD, development of rapidly progressive panlobular emphysema at a young age and reduction in lung function appear both in nonsmokers and smokers having severe genetic deficiencies. No genes other than the al-antitrypsin gene have been confirmed to be related to the pathogenesis of COPD, but attempts are being made to identify biomarkers of diseases through research on the basic cellular, molecular, and genetic abnormalities in COPD patients and to use the biomarkers for diagnosis or for discovery of new treatment methods (P. J. Barnes and R. A. Stockley. Eur. Respir. J. (2005) 25:1084-1106). In particular, research into diagnosis of COPD and selection of a treatment target through methods such as gene microarray or proteomics is being actively conducted. Analysis of genetic factors leading to COPD susceptibility and causes of exacerbation of COPD symptoms induced by smoking is mainly conducted (Peter J. Castaldi et al. Human Molecular Genetics, 2010, Vol. 19, No. 3 526-534).

Idiopathic pulmonary fibrosis (hereinafter referred to as 'IPF'), which is a kind of fibrosis, is a disease in which chronic inflammatory cells infiltrate the walls of the alveoli (pulmonary alveolus) and various changes that harden the lungs occur, causing severe structural changes in the lung tissue, gradually deteriorating lung function, and eventually leading to death. There is still no effective treatment method for IPF, and when IPF symptoms appear and the patients are diagnosed with IPF, the average survival time of the patients is only about 3 to 5 years, and thus, IPF is a disease with a very poor prognosis. In foreign countries, the incidence thereof is reported to be about 3-5 out of 100,000 persons, and it is known that the incidence rate is usually higher after the age of 50, and males are twice as likely to be diagnosed with the disease as females.

The etiology of IPF has not yet been clearly identified. It is common in smokers, and antidepressants, chronic lung inhalation due to gastroesophageal reflux, inhalation of metal dust, wood dust or solvents, and the like are reported to be risk factors associated with the occurrence of IPF. In most patients, however, no definitive causal factors have been reported. For the most frequently mentioned factors, whatever the cause, when Th1/Th2 responses, coagulation cascades, etc. are activated, it is known that fibrotic cytokines are secreted thereby and the activated cytokines stimulate fibroblasts to thus increase ECM (extracellular matrix) and cause pulmonary fibrosis. As such, this process is naturally accompanied by lung inflammation, which may lead to pulmonary fibrosis, but the opinion that pulmonary fibrosis is able to directly occur regardless of lung inflammation is more popular these days. A recent hypothesis is that pathological pulmonary fibrosis occurs during wound healing due to an abnormal signaling system of the epithelial-mesenchymal interaction. When epithelial cells are damaged, apoptosis of epithelial cells increases, migration thereof is restricted, differentiation thereof is not controlled, and proliferation is inhibited, so soluble factors (TGF, HGF, KGF, angiotensin II, ROS, etc.) are secreted and apoptosis of mesenchymal cells along with ECM is inhibited, resulting in increased myofibroblast differentiation, pulmonary fibrosis due to ECM deposition, or re-stimulation of epithelial cells. It cannot be said that lung inflammation directly causes pulmonary fibrosis, but it means that lung inflammation occurs first and then pulmonary fibrosis occurs due to the difference between IPF patients and normal people in the process of healing to restore normal tissue. In addition, IPF may be induced by Th1/Th2 cytokine imbalance. The Th1 cytokine response is related to cell-mediated immunity, which restores damaged tissue areas to normal tissue, whereas the Th2 cytokine induces ECM deposition and fibrosis through activation and proliferation of fibroblasts. It has been reported that, when IFN-$\gamma$ is administered to a bleomycin-induced pulmonary fibrosis model, it is able to prevent pulmonary fibrosis by reducing mRNA of TGF-$\beta$ and procollagen. However, since the etiology thereof is not exactly known, it is necessary to identify initial causative factors that cause fibrosis and to develop materials that are able to inhibit IPF-related genes and the TGF-β signaling system.

It is known that IPF continues to worsen without treatment, and about 50% or more of patients die within 3-5 years. In addition, once the disease has progressed and completely hardened into fibrosis, no matter what treatment is administered, there is no improvement. For treatment, it is predicted that there is a high probability of effectiveness if administered at an early stage. Although combination therapy of a steroid with azathioprine or cyclophosphamide is a known current treatment method, no remarkable effect is obtained thereby, and several fibrosis inhibitors have been tried in animal experiments and in a small number of patients, but none have been proven effective. In particular, in patients with end-stage IPF, there is no effective treatment method other than lung transplantation. Thus, there is an urgent need to develop a more effective therapeutic agent for IPF.

Fibrosis is a general term for a condition in which a tissue or organ becomes hard due to excessive fibrosis of the connective tissue for some reason, and all processes in which fibrosis occurs, regardless of the area, follow the same route as the process of scar healing. There are few cures for fibrosis symptoms to date, and treatment methods are under development and study. Effective fibrosis therapeutic agents may be applied not only to typical fibrosis, such as cirrhosis, liver fibrosis, myelofibrosis, myocardial fibrosis, renal fibrosis, and pulmonary fibrosis, but also to various diseases accompanied by fibrosis, so there is an urgent need to develop an effective therapeutic agent for fibrosis.

CTGF (connective tissue growth factor; CCN2) is a matricellular protein belonging to the CCN family, and is a secretory cytokine known to be involved in various biological processes such as cell adhesion, migration, proliferation, angiogenesis, wound repair, and the like, and overexpression of CTGF is deemed to be a major cause of symptoms such as scleroderma, fibrotic disease, and scarring (Brigstock D R. J. Cell Commun. Signal (2010) 4 (1): 1-4). In particular, in relation to fibrotic disease, CTGF is known to play a role in promoting the production of ECM (extracellular matrix) under conditions that induce either sustained fibrosis or fibrosis along with TGF-β growth factor-β, and in recent years, it is known that ocular disorders or muscular dystrophy caused by abnormal expression of CTGF may be treated using a sample or material that inhibits the expression of CTGF or the action thereof (U.S. Pat. No. 7,622,454, U.S. Patent Application Publication No. 20120164151).

As mentioned above, technological development for RNAi therapeutic agents for CTGF and delivery systems thereof is still insignificant, and the market demand for a double-stranded oligonucleotide therapeutic agent capable of specifically inhibiting CTGF expression with high efficiency and delivery technology therefor is very high.

Accordingly, the present inventors determined CTGF to be a gene related to respiratory diseases including COPD and fibrosis including IPF, selected a double-stranded oligonucleotide targeting CTGF, and verified an RNAi therapeutic agent capable of inhibiting CTGF expression and a delivery carrier thereof, thus culminating in the present invention.

DISCLOSURE

It is an object of the present invention to provide a double-stranded oligonucleotide capable of very specifically inhibiting the expression of CTGF with high efficiency, preferably a double-stranded oligonucleotide in the form of RNA/RNA, DNA/DNA, or DNA/RNA hybrid, most preferably a double-stranded oligonucleotide including the sequence in a DNA/RNA hybrid form, a double-stranded oligonucleotide construct including the double-stranded oligonucleotide, and nanoparticles including the double-stranded oligonucleotide or the double-stranded oligonucleotide construct.

It is another object of the present invention to provide a pharmaceutical composition for preventing or treating a respiratory disease and fibrosis containing the double-stranded oligonucleotide, the double-stranded oligonucleotide construct, and/or the nanoparticles as an active ingredient.

It is still another object of the present invention to provide a method of preventing or treating fibrosis or a respiratory disease including administering the double-stranded oligonucleotide, the double-stranded oligonucleotide construct, and/or the nanoparticles to a subject in need of prevention or treatment of fibrosis or a respiratory disease.

It is yet another object of the present invention to provide the use of the double-stranded oligonucleotide, the double-stranded oligonucleotide construct including the double-stranded oligonucleotide, and the nanoparticles including the double-stranded oligonucleotide or the double-stranded oligonucleotide construct for the prevention or treatment of fibrosis or a respiratory disease.

It is still yet another object of the present invention to provide the use of the pharmaceutical composition for the prevention or treatment of fibrosis or a respiratory disease.

It is a further object of the present invention to provide the use of the double-stranded oligonucleotide, the double-stranded oligonucleotide construct including the double-stranded oligonucleotide, and the nanoparticles including the double-stranded oligonucleotide or the double-stranded oligonucleotide construct for the manufacture of a medicament for the prevention or treatment of fibrosis or a respiratory disease.

In order to accomplish the above objects, the present invention provides a double-stranded oligonucleotide including a sense strand including any one sequence selected from the group consisting of SEQ ID NOs: 1 to 16, preferably any one sequence selected from the group consisting of SEQ ID NOs: 1, 2, 10, and 15, more preferably the sequence of SEQ ID NO: 10 and an antisense strand including a sequence complementary thereto.

In addition, the present invention provides a double-stranded oligonucleotide construct including the double-stranded oligonucleotide and nanoparticles including the double-stranded oligonucleotide or the double-stranded oligonucleotide construct.

In addition, the present invention provides a pharmaceutical composition for preventing or treating fibrosis or a respiratory disease, including a double-stranded oligonucleotide including a sense strand including any one sequence selected from the group consisting of SEQ ID NOs: 1 to 16, preferably any one sequence selected from the group consisting of SEQ ID NOs: 1, 2, 10, and 15, more preferably the sequence of SEQ ID NO: 10 and an antisense strand including a sequence complementary thereto, a double-stranded oligonucleotide construct including the double-stranded oligonucleotide, and/or nanoparticles including the double-stranded oligonucleotide or the double-stranded oligonucleotide construct.

In addition, the present invention provides a method of preventing or treating fibrosis or a respiratory disease including administering the double-stranded oligonucleotide, the double-stranded oligonucleotide construct, and/or the nanoparticles to a subject in need of prevention or treatment of fibrosis or a respiratory disease.

In addition, the present invention provides a method of preventing or treating fibrosis or a respiratory disease including administering the pharmaceutical composition for the prevention or treatment of fibrosis or a respiratory disease to a subject in need of prevention or treatment of fibrosis or a respiratory disease.

The double-stranded oligonucleotide including a sense strand including any one sequence selected from the group consisting of SEQ ID NOs: 1 to 16, preferably any one sequence selected from the group consisting of SEQ ID NOs: 1, 2, 10, and 15, more preferably the sequence of SEQ ID NO: 10 and an antisense strand including a sequence complementary thereto according to an aspect of the present invention, the double-stranded oligonucleotide construct including the double-stranded oligonucleotide, and/or the nanoparticles including the double-stranded oligonucleotide or the double-stranded oligonucleotide construct are capable of very efficiently inhibiting the expression of CTGF, so the double-stranded oligonucleotide, the double-stranded oligonucleotide construct, and the nanoparticles according to the present invention are useful for preventing or treating fibrosis or respiratory diseases.

The sequences of SEQ ID NOs: 1, 2, 10, and 15 included in the preferred double-stranded oligonucleotide that is provided in order to accomplish the above objects are as follows.

```
                                  (SEQ ID NO: 1)
5'-ATGTACAGTTATCTAAGTT-3'

                                  (SEQ ID NO: 2)
5'-TGTACAGTTATCTAAGTTA-3'

                                 (SEQ ID NO: 10)
5'-TGATTTCAGTAGCACAAGT-3'

                                 (SEQ ID NO: 15)
5'-TCAGTAGCACAAGTTATTT-3'
```

The double-stranded oligonucleotide according to the present invention is understood to include any material having general RNAi (RNA interference) action, and the mRNA-specific double-stranded oligonucleotide encoding the CTGF protein also includes CTGF-specific shRNA, as will be apparent to those skilled in the art to which the invention belongs. Simply put, the oligonucleotide may be siRNA, shRNA, or miRNA.

In addition, so long as specificity to CTGF is maintained, in the sense strand including any one sequence selected from the group consisting of SEQ ID NOs: 1, 2, 10, and 15 or in the antisense strand complementary thereto, CTGF-specific siRNA including the sense strand including the sequence in which at least one nucleotide is substituted, deleted, or inserted and the antisense strand thereof and antisense oligonucleotides are also included in the scope of the present invention, as will be apparent to those skilled in the art.

In the present invention, each of the sense strand and the antisense strand may independently be DNA or RNA, and a hybrid form in which the sense strand is DNA and the antisense strand is RNA or in which the sense strand is RNA and the antisense strand is DNA may be used.

In the present invention, SEQ ID NOs: 1, 2, 10, and 15 are described in the form of DNA, but when RNA is used, the sequences of SEQ ID NOs: 1, 2, 10, and 15 may be provided in the corresponding RNA sequence form in which T is changed to U.

Also, the double-stranded oligonucleotide according to the present invention includes not only a perfect match in which the sense strand of the sequence is a nucleotide sequence 100% complementary to the binding site of the CTGF gene, but also a mismatch in which some nucleotide sequences do not match, so long as specificity to CTGF is maintained.

The double-stranded oligonucleotide according to the present invention may include an overhang structure in which one or more unpaired nucleotides are provided at the 3' end of one or both strands.

In the present invention, the sense strand or the antisense strand is preferably composed of 19 to 31 nucleotides, but the present invention is not limited thereto.

In the present invention, the double-stranded oligonucleotide including a sense strand including any one sequence selected from the group consisting of SEQ ID NOs: 1, 2, 10, and 15 and an antisense strand including a sequence complementary thereto is specific to CTGF (connective tissue growth factor), but the present invention is not limited thereto.

In the present invention, the sense strand or the antisense strand of the double-stranded oligonucleotide includes any chemical modification in order to improve in-vivo stability or confer nuclease resistance and reduce nonspecific immune responses. The chemical modification may include, but is not limited to, at least one selected from the group consisting of a modification in which the hydroxyl group (—OH) at the 2' carbon position of the sugar structure in the nucleotide is substituted with any one selected from the group consisting of methyl (—$CH_3$), methoxy (—$OCH_3$), amine (—$NH_2$), fluorine (—F), O-2-methoxyethyl, O-propyl, O-2-methylthioethyl, O-3-aminopropyl, O-3-dimethylaminopropyl, O—N-methylacetamido, and O-dimethylamidooxyethyl; a modification in which oxygen of the sugar structure in the nucleotide is substituted with sulfur; a modification in which the nucleotide bond is any one bond selected from the group consisting of a phosphorothioate bond, a boranophosphate bond, and a methyl phosphonate bond; a modification into PNA (peptide nucleic acid), LNA (locked nucleic acid), or UNA (unlocked nucleic acid); and a modification in a DNA-RNA hybrid form (*Ann. Rev. Med.* 55, 61-65 2004; U.S. Pat. Nos. 5,660,985; 5,958,691; 6,531,584; 5,808,023; 6,326,358; 6,175,001; *Bioorg. Med. Chem. Lett.* 14:1139-1143, 2003; *RNA,* 9:1034-1048, 2003; *Nucleic Acid Res.* 31:589-595, 2003; *Nucleic Acids Research,* 38(17) 5761-773, 2010; *Nucleic Acids Research,* 39(5):1823-1832, 2011).

In the present invention, at least one phosphate group, preferably 1 to 3 phosphate groups, may be bound to the 5' end of the antisense strand of the double-stranded oligonucleotide.

Another aspect of the present invention pertains to a double-stranded oligonucleotide construct having the structure of Structural Formula (1) below, in which A is a hydrophilic material, B is a hydrophobic material, X and Y are each independently a simple covalent bond or a linker-mediated covalent bond, and R is a double-stranded oligonucleotide.

A-X—R—Y—B Structural Formula (1)

In a preferred embodiment, the double-stranded oligonucleotide construct including the CTGF-specific sequence according to the present invention has the structure of Structural Formula (1) below.

A-X—R—Y—B Structural Formula (1)

In Structural Formula (1), A is a hydrophilic material, B is a hydrophobic material, X and Y are each independently a simple covalent bond or a linker-mediated covalent bond, and R is a CTGF-specific double-stranded oligonucleotide.

The double-stranded oligonucleotide according to the present invention is preferably in the form of a DNA-RNA hybrid, siRNA (short interfering RNA), shRNA (short hairpin RNA), or miRNA (microRNA), but is not limited thereto, and also includes a single-stranded miRNA inhibitor that serves as an antagonist to miRNA.

Hereinafter, the double-stranded oligonucleotide according to the present invention will be described based on RNA, but may be applied to other double-stranded oligonucleotides (e.g. DNA/RNA hybrids) having the same properties as the double-stranded oligonucleotide of the present invention, as will be apparent to those skilled in the art.

More preferably, the double-stranded oligonucleotide construct including the CTGF-specific double-stranded oligonucleotide according to the present invention has the structure of Structural Formula (2) below.

Structural Formula (2)

A—X—S—Y—B
AS

In Structural Formula (2), A, B, X, and Y are as defined in Structural Formula (1), S represents the sense strand of the CTGF-specific nucleotide sequence, and AS represents the antisense strand of the CTGF-specific double-stranded oligonucleotide.

More preferably, the double-stranded oligonucleotide construct including the CTGF-specific double-stranded oligonucleotide has the structure of Structural Formula (3) or (4) below.

Structural Formula (3)

A—X—5′ S 3′—Y—B
AS

Structural Formula (4)

A—X—3′ S 5′—Y—B
AS

In Structural Formula (3) and Structural Formula (4), A, B, S, AS, X, and Y are as defined in Structural Formula (2), and 5' and 3' respectively represent the 5' end and the 3' end of the sense strand of the CTGF-specific double-stranded oligonucleotide.

The hydrophilic material may be selected from the group consisting of polyethylene glycol (PEG), polyvinylpyrrolidone, and polyoxazoline, but is not limited thereto.

In the double-stranded oligonucleotide construct including the CTGF-specific double-stranded oligonucleotide according to Structural Formula (1) to Structural Formula (4), one to three phosphate groups may be bound at the 5' end of the antisense strand, and shRNA may be used instead of RNA, as will be apparent to those skilled in the art.

The hydrophilic material in Structural Formula (1) to Structural Formula (4) is preferably a polymer material having a molecular weight of 200 to 10,000, more preferably a polymer material having a molecular weight of 1,000 to 2,000. For example, the hydrophilic polymer material may be a nonionic hydrophilic polymer compound such as polyethylene glycol, polyvinylpyrrolidone, polyoxazoline, etc., but is not necessarily limited thereto.

In particular, the hydrophilic material (A) in Structural Formula (1) to Structural Formula (4) may be used in the form of a hydrophilic material block represented by Structural Formula (5) or Structural Formula (6) below. When these hydrophilic material blocks are used in an appropriate number (n in Structural Formula (5) or Structural Formula (6)) depending on the need, problems due to polydispersity that may occur in the case of using general synthetic polymer materials, etc. may be greatly alleviated.

$(A'_m\text{-}J)_n$ Structural Formula (5)

$(J\text{-}A'_m)_n$ Structural Formula (6)

In Structural Formula (5), A' is a hydrophilic material monomer, J is a linker connecting m hydrophilic material monomers to each other or connecting m hydrophilic material monomers and an oligonucleotide to each other, m is an integer of 1 to 15, n is an integer of 1 to 10, and the repeating unit represented by $(A'_m\text{-}J)$ or $(J\text{-}A'_m)$ is the basic unit of the hydrophilic material block.

When the hydrophilic material block represented by Structural Formula (5) or Structural Formula (6) is provided, the double-stranded oligonucleotide construct including the CTGF-specific double-stranded oligonucleotide according to the present invention may have the structure of Structural Formula (7) or Structural Formula (8) below.

$(A'_m\text{-}J)_n$-X—R—Y—B Structural Formula (7)

$(J\text{-}A'_m)_n$—X—R—Y—B Structural Formula (8)

In Structural Formula (7) and Structural Formula (8), X, R, Y, and B are as defined in Structural Formula (1), and A', J, m, and n are as defined in Structural Formula (5) and Structural Formula (6).

In Structural Formula (5) and Structural Formula (6), any hydrophilic material monomer (A') may be used without limitation, so long as it meets the purpose of the present invention among the monomers of the nonionic hydrophilic polymer. Preferably, a monomer selected from among compound (1) to compound (3) shown in Table 1 below, more preferably a monomer of compound (1), is used, and G in compound (1) is preferably selected from among O, S, and NH.

In particular, among the hydrophilic material monomers, the monomer represented by compound (1) may be introduced with various functional groups, may exhibit superior biocompatibility such as having good in-vivo affinity and inducing less immune response, and may have the advantage of increasing the in-vivo stability of the double-stranded oligonucleotide contained in the construct according to Structural Formula (7) or Structural Formula (8) and increasing delivery efficiency, so it is very suitable for the production of the construct according to the present invention.

TABLE 1

| Structure of hydrophilic material monomer in the present invention | | |
|---|---|---|
| Compound (1) | Compound (2) | Compound (3) |
| 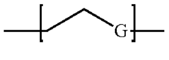 G being O, S, or NH | 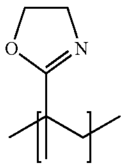 | 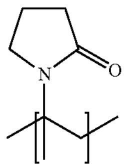 |

The hydrophilic material in Structural Formula (5) to Structural Formula (8) preferably has a total molecular weight in the range of 1,000 to 2,000. Thus, for example, in Structural Formula (7) and Structural Formula (8), when hexaethylene glycol according to compound (1), namely a material in which G is 0 and m is 6, is used, the molecular weight of the hexaethylene glycol spacer is 344, and thus the number of repetitions (n) is preferably 3 to 5. In particular, the repeating unit of the hydrophilic group represented by $(A'_m\text{-}J)_n$ or $(J\text{-}A'_m)_n$ in Structural Formula (5) and Structural Formula (6), namely the hydrophilic material block, may be used in an appropriate number represented by n, depending on the need. The hydrophilic material monomer A and the linker J included in each hydrophilic material block may be independently the same or different between hydrophilic material blocks. Specifically, when three hydrophilic material blocks are used (n=3), different hydrophilic material monomers may be used for respective hydrophilic material blocks, such as using the hydrophilic material monomer according to compound (1) for the first block, the hydrophilic material monomer according to compound (2) for the second block, and the hydrophilic material monomer according to compound (3) for the third block, or alternatively, any one hydrophilic material monomer selected from among the hydrophilic material monomers according to compounds (1) to (3) may be identically used for all of the hydrophilic material blocks. Likewise, as the linker that mediates the binding of the hydrophilic material monomers, the same or different linkers may be used for hydrophilic material blocks. Also, m, which is the number of hydrophilic material monomers, may be the same or different between hydrophilic material blocks. Specifically, different numbers of hydrophilic material monomers may be used in a manner in which three hydrophilic material monomers are linked (m=3) in the first hydrophilic material block, five hydrophilic material monomers are linked (m=5) in the second hydrophilic material block, and four hydrophilic material monomers are linked (m=4) in the third hydrophilic material block, or alternatively, the same number of hydrophilic material monomers may be used for all of the hydrophilic material blocks.

Also, in the present invention, the linker (J) is preferably selected from the group consisting of $—PO_3^-—$, $—SO_3—$, and $—CO_2—$, but is not limited thereto. Any linker may be used, so long as it meets the purpose of the present invention depending on the monomer of the hydrophilic material that is used, as will be apparent to those skilled in the art.

The hydrophobic material (B) in Structural Formula (1) to Structural Formula (4) and in Structural Formula (7) and Structural Formula (8) serves to form nanoparticles composed of the double-stranded oligonucleotide construct according to Structural Formula (1) to Structural Formula (4) and according to Formula (7) and Structural Formula (8) through hydrophobic interaction. The hydrophobic material preferably has a molecular weight of 250 to 1,000, and examples thereof may include, but are not limited to, a steroid derivative, glyceride derivative, glycerol ether, polypropylene glycol, $C_{12}$ to $C_{50}$ unsaturated or saturated hydrocarbon, diacylphosphatidylcholine, fatty acid, phospholipid, lipopolyamine, etc. Any hydrophobic material may be used, so long as it meets the purpose of the present invention, as will be apparent to those skilled in the art.

The steroid derivative may be selected from the group consisting of cholesterol, cholestanol, cholic acid, cholesteryl formate, cholestanyl formate, and colesteryl amine, and the glyceride derivative may be selected from among mono-, di-, and tri-glycerides. Here, the fatty acid of glyceride is preferably a $C_{12}$ to $C_{50}$ unsaturated or saturated fatty acid.

In particular, among examples of the hydrophobic material, a saturated or unsaturated hydrocarbon or cholesterol is preferable in that it facilitates binding in the step of synthesis of the double-stranded oligonucleotide construct according to the present invention, and a $C_{24}$ hydrocarbon, particularly a form including a disulfide bond, is most preferred.

The hydrophobic material is bound to the distal end of the hydrophilic material, and may be bound to any position of the sense strand or the antisense strand of siRNA.

The CTGF-specific double-stranded oligonucleotide and the hydrophilic or hydrophobic material in Structural Formula (1) to Structural Formula (4) and in Structural Formula (7) and Structural Formula (8) according to the present invention are bound through a simple covalent bond or a linker-mediated covalent bond (X or Y). The linker mediating the covalent bond is covalently bound to the hydrophilic material or the hydrophobic material at the end of the CTGF-specific double-stranded oligonucleotide, and is not particularly limited, so long as it provides a degradable bond in a certain environment, as necessary. Therefore, the linker may be any compound that binds to activate the CTGF-specific double-stranded oligonucleotide and/or the hydrophilic material (or the hydrophobic material) during the production of the double-stranded oligonucleotide construct according to the present invention. The covalent bond may be either a non-degradable bond or a degradable bond. Here, the non-degradable bond includes an amide bond or a phosphate bond, and the degradable bond includes a disulfide bond, an acid-degradable bond, an ester bond, an anhydride bond, a biodegradable bond, or an enzyme-degradable bond, but the present invention is not limited thereto.

In addition, the CTGF-specific double-stranded oligonucleotide represented by R (or S and AS) in Structural Formula (1) to Structural Formula (4) and in Structural Formula (7) and Structural Formula (8) may be used without limitation, so long as it is a double-stranded oligonucleotide capable of specifically binding to mRNA of CTGF. Preferably, in the present invention, it is composed of a sense strand including any one sequence selected from among SEQ ID NOs: 1, 2, 10, and and an antisense strand including a sequence complementary thereto.

In the double-stranded oligonucleotide construct including the CTGF-specific double-stranded oligonucleotide according to the present invention, an amine group or a polyhistidine group may be additionally introduced to the end of the hydrophilic material opposite the end to which the oligonucleotide is bound.

This facilitates the intracellular introduction of a carrier and endosomal escape by the double-stranded oligonucleotide construct including the CTGF-specific double-stranded oligonucleotide according to the present invention, and in order to facilitate the intracellular introduction of carriers such as quantum dots, dendrimers, and liposomes and endosomal escape, the introduction of an amine group and the use of a polyhistidine group and effects thereof have been reported.

Specifically, it is known that the primary amine group modified at the end or the outside of the carrier forms a conjugate through electrostatic interaction with a negatively charged gene while protonated at an in-vivo pH and also that the carrier may be protected from degradation of the lysosome because endosomal escape is facilitated due to the internal tertiary amine having a buffering effect at the low pH of the endosome after intracellular introduction (Gene transfer and expression inhibition using polymer-based hybrid material. *Polymer Sci. Technol., Vol.* 23, No. 3, pp 254-259).

It is known that histidine, which is a non-essential amino acid, has an imidazole ring ($pK_R$ 6.04) at the residue (-R), and thus increases buffering capacity in endosomes and lysosomes, so histidine modification may be used to increase endosomal escape efficiency in non-viral gene carriers, including liposomes (Novel histidine-conjugated galactosylated cationic liposomes for efficient hepatocyte selective gene transfer in human hepatoma HepG2 cells. J. Controlled Release 118, pp 262-270).

The amine group or polyhistidine group may be connected to the hydrophilic material or hydrophilic material block via at least one linker.

When an amine group or a polyhistidine group is introduced to the hydrophilic material of the double-stranded oligonucleotide construct according to Structural Formula (1) of the present invention, the structure represented by Structural Formula (9) below may be provided.

$P\text{-}J_1\text{-}J_2\text{-}A\text{-}X—R—Y—B$ Structural Formula (9)

In Structural Formula (9), A, B, R, X, and Y are as defined in Structural Formula (1).

Also, P is an amine group or a polyhistidine group, and $J_1$ and $J_2$ are linkers. Here, $J_1$ and $J_2$ may be independently selected from among a simple covalent bond, $PO_3^-$, $SO_3$, $CO_2$, $C_{2-12}$ alkyl, alkenyl, and alkynyl, but are not limited thereto, and any linker may be used as $J_1$ and $J_2$ meeting the purpose of the present invention depending on the hydrophilic material that is used, as will be apparent to those skilled in the art.

When an amine group is introduced, it is preferred that $J_2$ be a simple covalent bond or $PO_3^-$ and that $J_1$ be a $C_6$ alkyl, but the present invention is not limited thereto.

Also, when a polyhistidine group is introduced, in Structural Formula (9), it is preferred that $J_2$ be a simple covalent bond or $PO_3^-$ and that $J_1$ be compound (4), but the present invention is not limited thereto.

Compound (4)

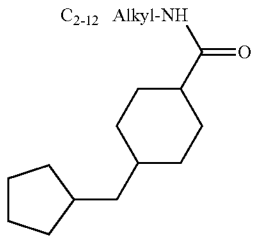

In addition, when the hydrophilic material of the double-stranded oligonucleotide construct according to Structural Formula (9) is a hydrophilic material block according to Structural Formula (5) or Structural Formula (6) and an amine group or polyhistidine group is introduced thereto, the structure represented by Structural Formula (10) or Structural Formula (11) below may be provided.

$P\text{-}J_1\text{-}J_2\text{-}(A'_m\text{-}J)_n\text{-}X—R—Y—B$ Structural Formula (10)

$P\text{-}J_1\text{-}J_2\text{-}(J\text{-}A'_m)_n\text{-}X—R—Y—B$ Structural Formula (11)

In Structural Formula (10) and Structural Formula (11), X, R, Y, B, A', J, m, and n are as defined in Structural Formula (5) or Structural Formula (6), and P, $J_1$, and $J_2$ are as defined in Structural Formula (9).

In particular, in Structural Formula (10) and Structural Formula (11), the hydrophilic material is preferably in a form bound to the 3' end of the sense strand of the CTGF-specific double-stranded oligonucleotide. Here, Structural Formula (9) to Structural Formula (11) may be represented by Structural Formula (12) to Structural Formula (14) below.

Structural Formula (12)

$P—J_1—J_2—A—X—3'\ S\ 5'—Y—B$
AS

Structural Formula (13)

$P—J_1—J_2\text{-}(A'_m—J)_n—X—3'\ S\ 5'—Y—B$
AS

Structural Formula (14)

$P—J_1—J_2—(J—A'_m)_n—X—3'\ S\ 5'—Y—B$
AS

In Structural Formula (12) to Structural Formula (14), X, R, Y, B, A, A' J, m, n, P, $J_1$, and $J_2$ are as defined in Structural Formula (9) to Structural Formula (11), and 5' and 3' respectively represent the 5' end and the 3' end of the sense strand of the CTGF-specific double-stranded oligonucleotide.

The amine group that may be introduced in the present invention may include primary to tertiary amine groups, particularly preferably a primary amine group. The amine group that is introduced may be provided in the form of an amine salt, and the salt of the primary amine group may be provided in the form of, for example, $NH_3^+$.

In addition, the polyhistidine group that may be introduced in the present invention may include 3 to 10 histidines, preferably 5 to 8 histidines, most preferably 6 histidines. Additionally, at least one cysteine may be included, in addition to histidine.

Meanwhile, when a targeting moiety is provided to the double-stranded oligonucleotide construct including the CTGF-specific double-stranded oligonucleotide according to the present invention and the nanoparticles formed therefrom, efficient delivery to a target cell may be promoted, and thus delivery thereof to a target cell is possible even at a relatively low concentration, thereby exhibiting a strong effect of regulating target gene expression and preventing a nonspecific CTGF-specific double-stranded oligonucleotide from being delivered to other organs and cells.

Accordingly, the present invention provides a double-stranded oligo RNA construct in which a ligand (L), particularly a ligand that specifically binds to a receptor that promotes target-cell internalization through receptor-mediated endocytosis (RME), is additionally bound to the construct according to Structural Formula (1) to Structural Formula (4) and according to Structural Formula (7) and Structural Formula (8). For example, the form in which a ligand is bound to the double-stranded oligo RNA construct according to Structural Formula (1) has the structure of Structural Formula (15) below.

$(L_i\text{-}Z)\text{-}A\text{-}X—R—Y—B$ Structural Formula (15)

In Structural Formula (15), A, B, X, and Y are as defined in Structural Formula (1), L is a ligand that specifically binds to a receptor that promotes target-cell internalization through receptor-mediated endocytosis (RME), and i is an integer of 1 to 5, preferably an integer of 1 to 3.

The ligand in Structural Formula (15) is preferably selected from among target-receptor-specific antibodies, aptamers, and peptides having RME properties that promote target-cell-specific cell internalization; and chemicals including folate (generally folate and folic acid are used interchangeably, and folate in the present invention refers to folate in a natural state or an activated state in the human body), hexosamines such as N-acetylgalactosamine (NAG), and sugars or carbohydrates such as glucose and mannose, but is not limited thereto.

Also, the hydrophilic material A in Structural Formula (15) may be used in the form of a hydrophilic material block according to Structural Formula (5) and Structural Formula (6).

Still another aspect of the present invention pertains to a method of producing a double-stranded oligonucleotide construct including a CTGF-specific double-stranded oligonucleotide.

The process of producing the double-stranded oligonucleotide construct including the CTGF-specific double-stranded oligonucleotide according to the present invention includes, for example:

(1) binding a hydrophilic material to a solid support;

(2) synthesizing a single-stranded oligonucleotide on the solid support to which the hydrophilic material is bound;

(3) covalently binding a hydrophobic material to the 5' end of the single-stranded oligonucleotide;

(4) synthesizing a single-stranded oligonucleotide having a sequence complementary to the sequence of the single-stranded oligonucleotide;

(5) separating and purifying an oligonucleotide/polymer construct and the single-stranded oligonucleotide from the solid support after completion of synthesis; and (6) producing a double-stranded oligonucleotide construct through annealing of the oligonucleotide/polymer construct and the single-stranded oligonucleotide having the complementary sequence.

The solid support in the present invention is preferably controlled pore glass (CPG), but is not limited thereto, and polystyrene (PS), polymethyl methacrylate (PMMA) silica gel, cellulose paper, etc. may be used. CPG preferably has a diameter of 40 to 180 μm and a pore size of 500 to 3000 Å. After step (5), the molecular weights of the purified RNA/polymer construct and single-stranded oligonucleotide are measured using a MALDI-TOF mass spectrometer to determine whether a desired oligonucleotide/polymer construct and single-stranded oligonucleotide are produced. In the production method described above, step (4) of synthesizing a single-stranded oligonucleotide having a sequence complementary to the sequence of the single-stranded oligonucleotide synthesized in step (2) may be performed before step (1) or during any one of steps (1) to (5).

Also, the single-stranded oligonucleotide having the sequence complementary to the sequence of the single-stranded oligonucleotide synthesized in step (2) may be used in a form in which a phosphate group is bound to the 5' end.

In addition, there is provided a method of producing a double-stranded oligonucleotide construct in which a ligand is additionally bound to the double-stranded oligonucleotide construct including the CTGF-specific double-stranded oligonucleotide according to the present invention.

The method of producing the ligand-bound double-stranded oligonucleotide construct including the CTGF-specific double-stranded oligonucleotide includes, for example:

(1) binding a hydrophilic material to a solid support to which a functional group is bound;

(2) synthesizing a single-stranded oligonucleotide on the solid support to which the functional group and the hydrophilic material are bound;

(3) covalently binding a hydrophobic material to the 5' end of the single-stranded oligonucleotide;

(4) synthesizing a single-stranded oligonucleotide having a sequence complementary to the sequence of the single-stranded oligonucleotide;

(5) separating a functional-group/oligonucleotide/polymer construct and the single-stranded oligonucleotide having the complementary sequence from the solid support after completion of synthesis;

(6) producing a ligand/oligonucleotide/polymer construct in the form of a single strand by binding a ligand to the end of the hydrophilic material using the functional group; and (7) producing a ligand/double-stranded-oligonucleotide construct through annealing of the ligand/oligonucleotide/polymer construct and the single-stranded oligonucleotide having the complementary sequence.

After step (6), the produced ligand/oligonucleotide/polymer construct and the single-stranded oligonucleotide having the complementary sequence are separated and purified, and the molecular weights thereof are then measured using a MALDI-TOF mass spectrometer to determine whether a desired ligand/oligonucleotide/polymer construct and complementary oligonucleotide are produced. The ligand/double-stranded oligonucleotide construct may be produced through annealing of the ligand/oligonucleotide/polymer construct and the single-stranded oligonucleotide having the complementary sequence. In the production method described above, step (4) of synthesizing a single-stranded oligonucleotide having the sequence complementary to the sequence of the single-stranded oligonucleotide synthesized in step (3) may be an independent synthesis process, and may be performed before step (1) or during any one of steps (1) to (6).

Yet another aspect of the present invention pertains to nanoparticles including the double-stranded oligonucleotide construct according to the present invention. The double-stranded oligonucleotide construct according to the present invention forms self-assembled nanoparticles through hydrophobic interaction of the hydrophobic material (Korean Patent No. 1224828). These nanoparticles not only have vastly superior delivery efficiency into the body and in-vivo stability, but also have excellent particle size uniformity, which facilitates quality control (QC), thereby simplifying the process of manufacture into a drug.

In the present invention, the nanoparticles may be characterized in that double-stranded oligonucleotide constructs including double-stranded oligonucleotides including different sequences are mixed. In one embodiment, the nanoparticles may include one type of CTGF-specific double-stranded oligonucleotide including a sense strand including any one sequence selected from among SEQ ID NOs: 1, 2, 10, and 15 and an antisense strand including a sequence complementary thereto, and in another embodiment, the nanoparticles may include different types of CTGF-specific double-stranded oligonucleotides including a sense strand including any one sequence selected from among SEQ ID NOs: 1, 2, 10, and 15 and an antisense strand including a sequence complementary thereto, and may also include a CTGF-specific double-stranded oligonucleotide not disclosed in the present invention.

Still yet another aspect of the present invention pertains to a pharmaceutical composition for preventing or treating fibrosis or a respiratory disease containing the double-stranded oligonucleotide, the double-stranded oligonucleotide construct, or the nanoparticles according to the present invention as an active ingredient.

The pharmaceutical composition for the prevention or treatment of fibrosis or a respiratory disease according to the present invention inhibits connective tissue remodeling, particularly pulmonary artery remodeling and airway remodeling, and is thus effective at preventing or treating fibrosis or a respiratory disease.

In the present invention, the respiratory disease may be chronic obstructive pulmonary disease (COPD), asthma, acute and chronic bronchitis, allergic rhinitis, productive cough, bronchitis, bronchiolitis, laryngopharyngitis, tonsillitis, or laryngitis, and the fibrosis may be selected from among idiopathic pulmonary fibrosis (IPF), liver fibrosis, cirrhosis, myelofibrosis, myocardial fibrosis, renal fibrosis, keloid, pulmonary fibrosis, cardiac fibrosis, and radiation-induced fibrosis, but the present invention is not limited thereto. In the present invention, the radiation-induced fibrosis is a side effect frequently induced by radiation therapy commonly used for the treatment of cancer, tumors, etc., and may be used interchangeably with radiation fibrosis syndrome (RFS).

The composition of the present invention may be prepared by including at least one pharmaceutically acceptable carrier in addition to the active ingredient described above for administration. The pharmaceutically acceptable carrier must be compatible with the active ingredient of the present invention, and may include saline, sterile water, Ringer's solution, buffered saline, dextrose solution, maltodextrin solution, glycerol, and ethanol, which may be used alone or in combinations of two or more thereof. Other typical additives such as antioxidants, buffers, and bacteriostats may be added as necessary. Also, diluents, dispersants, surfactants, binders, and lubricants may be additionally added to form an injectable formulation such as an aqueous solution, suspension, emulsion, and the like. In particular, it is preferable to provide a lyophilized formulation. For the preparation of the lyophilized formulation, a method commonly known in the art to which the present invention belongs may be used, and a stabilizer for lyophilization may be added. Preferably, it is possible to prepare a formulation depending on each disease or component using an appropriate method in the art or a method disclosed in Remington's Pharmaceutical Science (Mack Publishing Company, Easton PA).

The type of composition of the present invention may be determined by those skilled in the art based on the symptoms of a typical patient and the severity of the disease. In addition, it may be formulated in various forms such as powders, tablets, capsules, solutions, injections, ointments, syrups, and the like, and may be provided in unit-dose or multiple-dose containers, for example, sealed ampoules and bottles.

The composition of the present invention may be administered orally or parenterally. The route of administration of the composition according to the present invention is not limited thereto, and for example, oral, inhalational, intravenous, intramuscular, intraarterial, intramedullary, intradural, intracardiac, transdermal, subcutaneous, intraperitoneal, enteral, sublingual, or topical administration is possible. In particular, for treatment of a respiratory disease, administration to the lungs through endobronchial instillation is also possible. The dosage of the composition according to the present invention varies depending on the patient's body weight, age, gender, health status, diet, administration time, method, excretion rate, severity of disease, etc., and may be easily decided by those skilled in the art. Moreover, the composition of the present invention may be formulated into a suitable dosage form for clinical administration using known techniques.

Even still yet another aspect of the present invention pertains to a lyophilized formulation including the pharmaceutical composition according to the present invention.

A further aspect of the present invention pertains to a method of preventing or treating fibrosis or a respiratory disease including administering the pharmaceutical composition for the prevention or treatment of fibrosis or a respiratory disease according to the present invention to a subject in need of prevention or treatment of fibrosis or a respiratory disease.

In the present invention, the respiratory disease may be chronic obstructive pulmonary disease (COPD), asthma, acute and chronic bronchitis, allergic rhinitis, productive cough, bronchitis, bronchiolitis, laryngopharyngitis, tonsillitis, or laryngitis, and the fibrosis may be idiopathic pulmonary fibrosis (IPF), cirrhosis, myelofibrosis, myocardial fibrosis, renal fibrosis, keloid, pulmonary fibrosis, cardiac fibrosis, liver fibrosis, or radiation-induced fibrosis, but the present invention is not limited thereto.

Still a further aspect of the present invention pertains to the use of the double-stranded oligonucleotide, the double-stranded oligonucleotide construct including the double-stranded oligonucleotide, and the nanoparticles including the same for the prevention or treatment of fibrosis or a respiratory disease.

Yet a further aspect of the present invention pertains to the use of the pharmaceutical composition for the prevention or treatment of fibrosis or a respiratory disease.

Still yet a further aspect of the present invention pertains to the use of the double-stranded oligonucleotide, the double-stranded oligonucleotide construct including the double-stranded oligonucleotide, and the nanoparticles including the double-stranded oligonucleotide or the double-stranded oligonucleotide construct for the prevention or treatment of fibrosis or a respiratory disease.

Even still a further aspect of the present invention pertains to a method of preventing or treating fibrosis or a respiratory disease including administering the double-stranded oligonucleotide, the double-stranded oligonucleotide construct, and/or the nanoparticles to a subject in need of prevention or treatment of fibrosis or a respiratory disease.

Even yet a further aspect of the present invention pertains to the use of the double-stranded oligonucleotide, the double-stranded oligonucleotide construct including the double-stranded oligonucleotide, and the nanoparticles including the double-stranded oligonucleotide or the double-stranded oligonucleotide construct for the manufacture of a medicament for the prevention or treatment of fibrosis or a respiratory disease.

MODE FOR INVENTION

Figure 1:
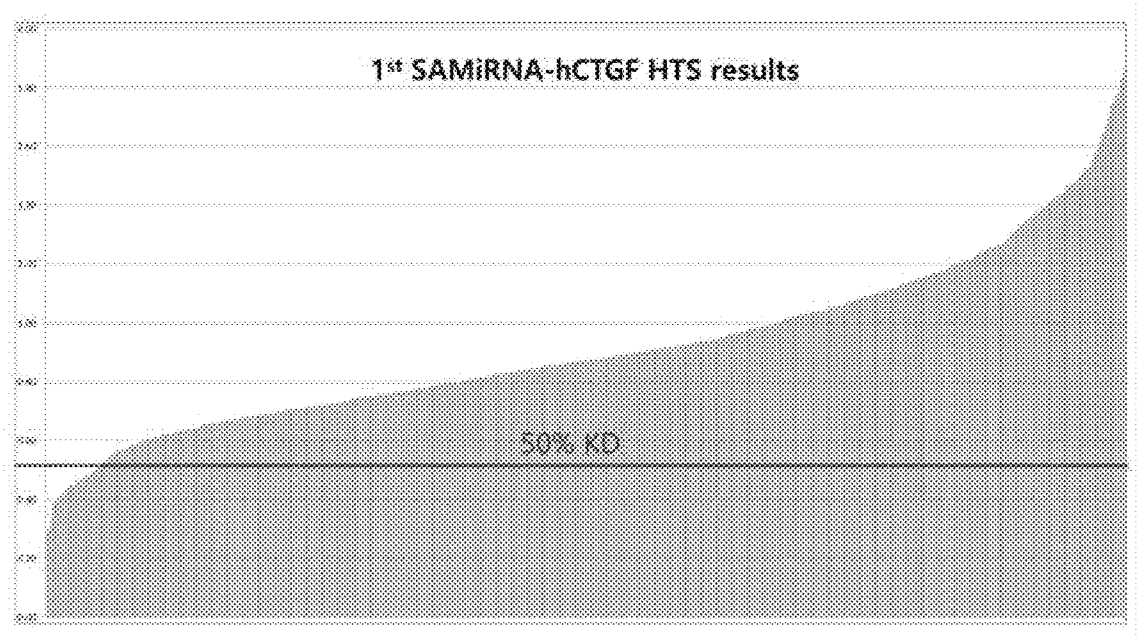
FIG. 1 shows the results of screening of 1,162 SAMiRNAs targeting human CTGF, including the results of quantitative analysis of the mRNA expression level of CTGF in Example 3.

A better understanding of the present invention may be obtained through the following examples. These examples are merely set forth to illustrate the present invention and are not construed as limiting the scope of the present invention, as will be apparent to those skilled in the art. Therefore, the substantial scope of the present invention will be defined by the appended claims and equivalents thereof.

In the present invention, it was confirmed that a specific sequence capable of inhibiting the expression of CTGF was ultimately identified and CTGF expression was effectively inhibited by complementary binding thereof to mRNA encoding CTGF, thereby effectively treating fibrosis and respiratory diseases.

Example 1. Algorithm for Screening of SAMiRNA Targeting CTGF and Selection of Candidate Sequences SAMiRNA-based drug high-throughput screening is a method for generating all possible candidate sequences by applying a 1-base or 2-base sliding-window algorithm to an entire mRNA sample, removing unnecessary candidate sequences by performing homology filtering, and determining the extent of inhibition of expression of the corresponding gene by all of the finally selected SAMiRNAs.

A design process for SAMiRNA candidate sequences for CTGF was performed in a manner in which a 2-base sliding-window algorithm was applied to NM_001901.2 (2,358 bp), which is human CTGF mRNA, to thus finally select 1,162 SAMiRNA candidate sequences each composed of 19 nucleotides, and the extent of inhibition of CTGF thereby was evaluated.

Example 2. Synthesis of Double-Stranded Oligo RNA Construct

The double-stranded oligo RNA construct (SAMiRNA) produced in the present invention has a structure according to the following structural formula.

$C_{24}$-5'S 3'-(hexaethyleneglycol-$PO_4^-$)$_3$-hexaethyleneglycol

AS 5'-PO4

The sense strand of a monoSAMiRNA (n=4) double-stranded oligo construct was synthesized in a manner in which three dimethoxytrityl (DMT) hexaethylene glycol phosphoramidates, which are hydrophilic material monomers, were successively bound through the above reaction using 3,4,6-triacetyl-1-hexa(ethyleneglycol)-N-acetyl galactosamine-CPG as a support, RNA or DNA synthesis was performed, and then $C_{24}$($C_6$—S—S—$C_{18}$) containing a disulfide bond, which is a hydrophobic material, was bound to the 5' end, thereby obtaining the sense strand of monoSAMiRNA (n=4) in which NAG-hexaethylene glycol-(—$PO_3$-hexaethylene glycol) 3 was bound to the 3' end and $C_{24}$ ($C_6$—S—S—$C_{18}$) was bound to the 5' end.

After completion of synthesis, the synthesized single-stranded RNA and oligo (DNA or RNA)/polymer construct were separated from CPG using 28% (v/v) ammonia in a water bath at 60° C., followed by a deprotection reaction to remove protective residues. After removal of the protective residues, the single-stranded RNA and the oligo (DNA or RNA)/polymer construct were treated with N-methylpyrrolidone, triethylamine, and triethylamine trihydrofluoride at a volume ratio of 10:3:4 in an oven at 70° C. to remove 2'-dimethylsilyl. The single-stranded RNA, the oligo (DNA or RNA)/polymer construct, and the ligand-bound oligo (DNA or RNA)/polymer construct were separated from the reaction products through high-performance liquid chromatography (HPLC), and the molecular weights thereof were measured using a TOF mass spectrometer (MALDI TOF- MS, SHIMADZU, Japan) to determine whether they matched the nucleotide sequence and the oligo/polymer construct to be synthesized. Thereafter, in order to produce each double-stranded oligo construct, the sense strand and the antisense strand were mixed in equal amounts, added to a 1× annealing buffer (30 mM HEPES, 100 mM potassium acetate, 2 mM magnesium acetate, pH 7.0), allowed to react in a constant-temperature water bath at 90° C. for 3 minutes, and allowed to react at 37° C. again, thereby producing desired SAMiRNA. Annealing of the double-stranded oligo RNA constructs thus produced was confirmed through electrophoresis.

Example 3. High-Throughput Screening (HTS) of SAMiRNA Nanoparticles Inducing RNAi Targeting Human CTGF 3.1 Production of SAMiRNA Nanoparticles 1,162 SAMiRNAs targeting the CTGF sequence synthesized in Example 2 were dissolved in 1× Dulbecco's phosphate-buffered saline (DPBS) (WELGENE, KR) and lyophilized for 5 days in a freeze dryer (LGJ-100F, CN). The lyophilized nanoparticle powder was dissolved and homogenized in 1.429 ml of deionized distilled water (Bioneer, KR) and used in the experiments for the present invention.

3.2 Intracellular Processing of SAMiRNA Nanoparticles

MDA-MB231, which is a human-derived breast cancer cell line, was used to discover SAMiRNA that inhibits CTGF expression, and the MDA-MB231 cell line was cultured at 37° C. and 5% $CO_2$ in a Gibco™ RPMI 1640 medium (Thermo, US) containing 10% fetal bovine serum (Hyclone, US) and 1% penicillin-streptomycin (Hyclone, US). Using the same medium as above, the MDA-MB231 cell line was dispensed at a density of $2\times10^4$ cells/well in a 96-well plate (Costar, US), and the next day, SAMiRNA homogenized with deionized distilled water in Example 3.1 was diluted to 200 nM or 600 nM with 1×DPBS and added to the cells. Cell treatment with SAMiRNA was performed a total of 4 times, once every 12 hours, and culture was carried out at 37° C. and 5% $CO_2$.

3.3 SAMiRNA Screening Through Analysis of CTGF mRNA Expression Inhibitory Efficacy Total RNA was extracted from the cell line treated with SAMiRNA in Example 3-2 and was synthesized into cDNA, after which the relative mRNA expression level of the CTGF gene was quantified using real-time PCR.

In order to analyze the mRNA expression level of the CTGF gene, a 300 nM CTGF forward primer, a 300 nM CTGF reverse primer, a 300 nM CTGF probe, a 200 nM RPL13A forward primer, a 200 nM RPL13A reverse primer, a 300 nM RPL13A probe, a 400 nM TBP forward primer, a 400 nM TBP reverse primer, and a 300 nM TBP probe were added to each well of an AccuPower® Dual-HotStart RT-qPCR kit (Bioneer, Korea) and dried (Table 2). The performance of the prepared kit was determined based on PCR amplification efficiency (Table 3) by creating a calibration curve using A549 cell total RNA. RT-qPCR was performed under reaction conditions of 95° C. for 10 minutes and then (95° C. for 5 seconds and 58° C. for 15 seconds)×45 cycles, and a protocol in which the fluorescence value was detected at each cycle was followed.

The SAMiRNA-treated 96-well plate (Costar, US) was subjected to total RNA extraction and one-step RT-qPCR according to an automated program using ExiStation HT™ Korea, which is an automated apparatus that performs all procedures from total RNA extraction to RT-qPCR, an HT DNA/RNA extraction kit (Bioneer, Korea), and an AccuPower® Dual-HotStart RT-qPCR kit (Bioneer, Korea) that is separately prepared by including primers and probes for quantitative analysis of CTGF gene mRNA.

Based on the Ct values of two genes obtained after qPCR array, the relative mRNA expression level (%) of the CTGF gene in the experimental group compared to the control group was calculated through relative quantitative analysis using a 2(−Delta Delta C(T)) method [Livak K. J., Schmittgen T. D. 2001. Analysis of relative gene expression data using real-time quantitative PCR and the 2(−Delta Delta C(T)) Method. Methods. Dec; 25(4):402-8].

TABLE 2

| Primer and hydrolysis probe sequences used in high-throughput screening (HTS) | |
|---|---|
| CTGF Forward primer | CACCAGCATGAAGACATACCG (SEQ ID NO: 33) |
| CTGF Reverse primer | CGTCAGGGCACTTGAACTC (SEQ ID NO: 34) |
| CTGF probe | 5'FAM-CCGACGGCCGATGCTGCACCCCC-3'EBQ (SEQ ID NO: 35) |
| RPL13A Forward primer | GTGTTTGACGGCATCCCACC (SEQ ID NO: 36) |
| RPL13A Reverse primer | TAGGCTTCAGACGCACGACC (SEQ ID NO: 37) |
| RPL13A probe | 5'TAMRA-AAGCGGATGGTGGTTCCTGCT-3'EBQ (SEQ ID NO: 38) |
| TBP Forward primer | CACCACAGCTCTTCCACTC (SEQ ID NO: 39) |
| TBP Reverse primer | ATCCCAGAACTCTCCGAAGC (SEQ ID NO: 40) |
| TBP probe | 5'TEXASRED-ACCCTTGCCGGGCACCACTC-3'EBQ (SEQ ID NO: 41) |

TABLE 3

| 3-plex RT-qPCR amplification efficiency | | | |
|---|---|---|---|
| Name | Slope | $R^2$ | Efficiency |
| CTGF | Y = −0.3020X + 7.6316 | 0.9966 | 100% |
| RPL13A | Y = −0.2977X + 7.4425 | 0.9997 | 98% |
| TBP | Y = −0.2958X + 10.5934 | 0.9952 | 99% |

Example 4. Screening of SAMiRNA Nanoparticles Inducing RNAi Targeting Human CTGF In order to select highly efficient SAMiRNA, a lung cancer cell line A549 was treated with sequences having the highest efficiency of reduction of the mRNA expression level of CTGF at a final concentration of 200 nM or 600 nM compared to the control group, namely 16 sequences having reduction efficiency>60% or more (secondary screening results for a total of 49 types of SAMiRNA-hCTGF), at concentrations of 500 nM and 1000 nM, and the sequence information of the corresponding SAMiRNA is shown in Table 4 below.

Thereafter, in order to proceed with an experiment to confirm the effect of reduction of expression level (knockdown) after treatment at a low concentration to determine $IC_{50}$ compared to Rxi-109 (sense: 5'-GCACCUUUCUA*G*A-chol-3' (SEQ ID NO: 57) 13mer/AS: 5'-phosphate-UCUAGAAAGGUGC*A*A*A*C*A*U-3' (SEQ ID NO: 58) 19mer/bold=2'OME/underline=2'F/asterisk=phosphorothioate/chol=cholesterol) (WO 2009/102427), tertiary screening of the lung cancer cell line A549 for the eight strongest sequences was performed at 50, 100, 200, 500, and 1000 nM. Consequently, four SAMiRNAs having the sequences of SEQ ID NOs: 1, 2, 10, and 15 as respective sense strands were selected.

Figure 2:
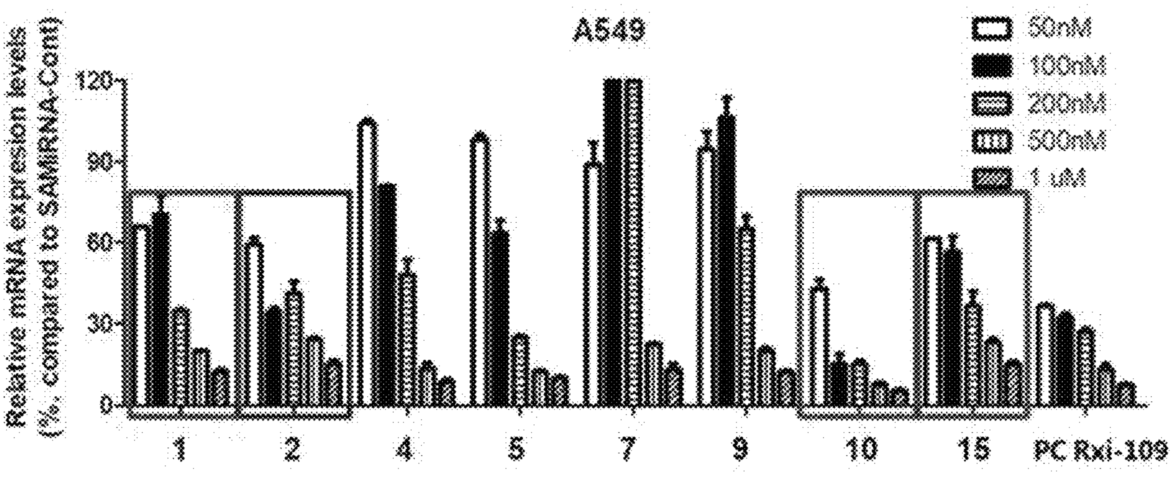
FIG. 2 is a graph showing the results of quantitative analysis of the mRNA expression level of CTGF in Example 4, in which the relative mRNA expression level (%) of CTGF was determined after treatment of a lung cancer cell line A549 with SAMiRNA having, as a sense strand, each of the sequences of SEQ ID NOs: 1, 2, 10, and 15 of the present invention at different concentrations (50, 100, 200, 500, and 1000 nM)

As shown in FIG. 1, the four SAMiRNAs that inhibit CTGF gene expression most effectively were finally selected from among 1,162 SATiRNAs targeting CTGF (FIG. 2).

TABLE 4

CTGF-specific SAMiRNA candidate sequences selected through 2-base sliding-window screening and high-throughput screening (HTS)

| SEQ ID NO: | Accession No. | Position | Sequence (DNA/RNA) | |
|---|---|---|---|---|
| 1 | NM_001901.2 | 1890-1908 | Sense | ATGTACAGTTATCTAAGTT |
| 17 | | | Antisense | AACUUAGAUAACUGUACAU |
| 2 | NM_001901.2 | 1891-1909 | Sense | TGTACAGTTATCTAAGTTA |
| 18 | | | Antisense | UAACUUAGAUAACUGUACA |
| 3 | NM_001901.2 | 1982-2000 | Sense | GTACAGTTATCTAAGTTAA |
| 19 | | | Antisense | UUAACUUAGAUAACUGUAC |
| 4 | NM_001901.2 | 2042-2060 | Sense | ATGGAAATTCTGCTCAGAT |
| 20 | | | Antisense | AUCUGAGCAGAAUUUCCAU |
| 5 | NM_001901.2 | 2043-2061 | Sense | TGGAAATTCTGCTCAGATA |
| 21 | | | Antisense | UAUCUGAGCAGAAUUUCCA |
| 6 | NM_001901.2 | 2044-2062 | Sense | GGAAATTCTGCTCAGATAG |
| 22 | | | Antisense | CUAUCUGAGCAGAAUUUCC |
| 7 | NM_001901.2 | 1332-1350 | Sense | ATTTCAGTAGCACAAGTTA |
| 23 | | | Antisense | UAACUUGUGCUACUGAAAU |
| 8 | NM_001901.2 | 1333-1351 | Sense | TTTCAGTAGCACAAGTTAT |
| 24 | | | Antisense | AUAACUUGUGCUACUGAAA |
| 9 | NM_001901.2 | 1334-1352 | Sense | TTCAGTAGCACAAGTTATT |
| 25 | | | Antisense | AAUAACUUGUGCUACUGAA |
| 10 | NM_001901.2 | 1330-1348 | Sense | TGATTTCAGTAGCACAAGT |
| 26 | | | Antisense | ACUUGUGCUACUGAAAUCA |
| 11 | NM_001901.2 | 1331-1349 | Sense | GATTTCAGTAGCACAAGTT |
| 27 | | | Antisense | AACUUGUGCUACUGAAAUC |
| 12 | NM_001901.2 | 1324-1342 | Sense | TAAAAATGATTTCAGTAGC |
| 28 | | | Antisense | GCUACUGAAAUCAUUUUUA |
| 13 | NM_001901.2 | 1325-1343 | Sense | AAAAATGATTTCAGTAGCA |
| 29 | | | Antisense | UGCUACUGAAAUCAUUUUU |
| 14 | NM_001901.2 | 1326-1344 | Sense | AAAATGATTTCAGTAGCAC |
| 30 | | | Antisense | GUGCUACUGAAAUCAUUUU |
| 15 | NM_001901.2 | 1335-1353 | Sense | TCAGTAGCACAAGTTATTT |
| 31 | | | Antisense | AAAUAACUUGUGCUACUGA |
| 16 | NM_001901.2 | 1336-1354 | Sense | CAGTAGGAGAAGTTATTTA |
| 32 | | | Antisense | UAAAUAACUUGUGCUACUG |

The lung cancer cell line A549 was treated with SAMiRNA having, as the sense strand, each of the sequences of SEQ ID NOs: 1, 2, 10, and 15 selected in Example 3, and the mRNA expression pattern of CTGF in the cell line was analyzed.

4.1 Intracellular Processing of SAMiRNA Nanoparticles

A549 (ATCC® CCL-185™, Manassas, VA), which is a human-derived lung cancer cell line, was used to discover SAMiRNA that inhibits CTGF expression, and the A549 cell line was cultured at 37° C. and 5% $CO_2$ in a Gibco™F-12K (Kaighn's) medium (Thermo, US) containing 10% fetal bovine serum (Hyclone, US) and 1% penicillin-streptomycin (Hyclone, US). Using the same medium as above, the A549 cell line was dispensed at a density of $8\times10^4$ cells/well in a 12-well plate (Costar, US), and the next day, SAMiRNA homogenized with deionized distilled water in Example 3.1 was diluted to 50, 100, 200, 500, or 1000 nM with 1×DPBS and added to the cells. Cell treatment with SAMiRNA was performed a total of 4 times, once every 12 hours, and culture was carried out at 37° C. and 5% $CO_2$.

4.2 SAMiRNA Screening Through Analysis of Human CTGF mRNA Expression Inhibitory Efficacy Total RNA was extracted from the cell line treated with SAMiRNA in Example 4-1 and was synthesized into cDNA, and then the relative mRNA expression level of the CTGF gene was quantified using real-time PCR.

4-2-1 RNA Isolation from SAMiRNA-Treated Cells and cDNA Synthesis

Total RNA was extracted from the cell line treated with SAMiRNA in Example 4-1 using an RNA extraction kit (AccuPrep Cell total RNA extraction kit, Bioneer, Korea), and the extracted RNA was synthesized into cDNA using RNA reverse transcriptase (AccuPower® RocketScript™ Cycle RT Premix with oligo (dT)20, Bioneer, Korea) in the following manner. Specifically, 1 μg of the extracted RNA was added to AccuPower RocketScript™RT Premix with oligo (dT) 20 (Bioneer, Korea) contained in each of 0.25 ml Eppendorf tubes, and DEPC (diethyl pyrocarbonate)-treated distilled water was added thereto to achieve a total volume of 20 μl. In a gene amplification system (MyGenie™ Gradient Thermal Block, Bioneer, Korea), two processes of hybridizing RNA with primers at 37° C. for 30 seconds and synthesizing cDNA at 48° C. for 4 minutes were repeated 12 times, after which the amplification reaction was terminated by deactivating the enzyme at 95° C. for 5 minutes.

4-2-2 Relative Quantitative Analysis of Human CTGF mRNA

The relative mRNA expression level of CTGF compared to the SAMiRNA control sample was analyzed in the following manner through SYBR green real-time qPCR using the cDNA synthesized in Example 4-2-1 as a template. Specifically, the cDNA synthesized in Example 4-2-1 was diluted 5-fold with distilled water, and for analysis of the mRNA expression level of CTGF, 3 μl of the diluted cDNA, 25 μl of AccuPower® GreenStar™ (Korea), 19 μl of distilled water, and 3 μl of CTGF qPCR primers (SEQ ID NOs: 7 and 8 (Table 5); 10 pmol/μl, respectively, Bioneer, Korea) were added to each well of a 96-well plate to obtain a mixed solution. Meanwhile, in order to normalize the mRNA expression level of CTGF, GAPDH (glyceraldehyde-3-phosphate dehydrogenase), which is a housekeeping (HK) gene, was used as a standard gene. The 96-well plate containing the mixed solution was subjected to the following reaction using an Exicycler™ Real-Time Quantitative Thermal Block (Bioneer, Korea): reaction at 95° C. for 15 minutes to activate the enzyme and remove the secondary structure of cDNA, 42 cycles each including four processes of denaturation at 94° C. for 30 seconds, annealing at 58° C. for 30 seconds, extension at 72° C. for 30 seconds, and SYBR green scan, and final extension at 72° C. for 3 minutes, after which the temperature was maintained at 55° C. for 1 minute and the melting curve from 55° C. to 95° C. was analyzed.

After termination of PCR, the Ct (threshold cycle) value of each target gene was corrected using the GAPDH gene, and then a difference ΔCt in Ct values was calculated using a control group treated with SAMiRNA (SAMiCONT) (sense: 5'-CUUACGCUGAGUACUUCGA-3' (19mer) (SEQ ID NO: 59), antisense: 5'-UCGAAGUACUCAGCGUAAG-3' (19mer) (SEQ ID NO: 60)), which is a control sequence that does not induce gene expression inhibition. The relative expression level of the target gene in the cells treated with CTGF-specific SAMiRNA was quantified using the ΔCt value and equation 2 (−ΔCtx100).

In order to select highly efficient SAMiRNA, SAMiRNA #10, having, as the sense strand, the sequence having the highest efficiency of reduction of the mRNA expression level of CTGF at a final concentration of 50, 100, 200, 500, or 1000 nM compared to the control group, namely the sequence of SEQ ID NO: 10, was finally selected.

Figure 3:
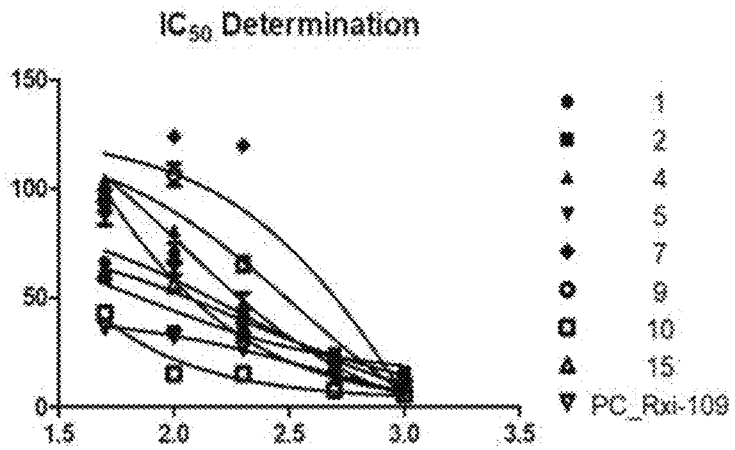
FIG. 3 is a graph showing the results of quantitative analysis of the mRNA expression level of CTGF in Example 4, in which the $IC_{50}$ value of SAMiRNA was determined by analyzing the relative mRNA expression level (%) of CTGF after treatment of the lung cancer cell line A549 with SAMiRNA having, as a sense strand, the sequence of SEQ ID NO: 10 of the present invention at different concentrations.

As shown in FIG. 3, SAMiRNA #10, which inhibits CTGF gene expression most effectively, was finally selected from among eight SAMiRNAs targeting CTGF, and the $IC_{50}$ value of SAMiRNA was determined by analyzing the mRNA expression pattern of CTGF in the cell line. The sequence information of the corresponding SAMiRNA is shown in Table 6 below.

Figure 4:
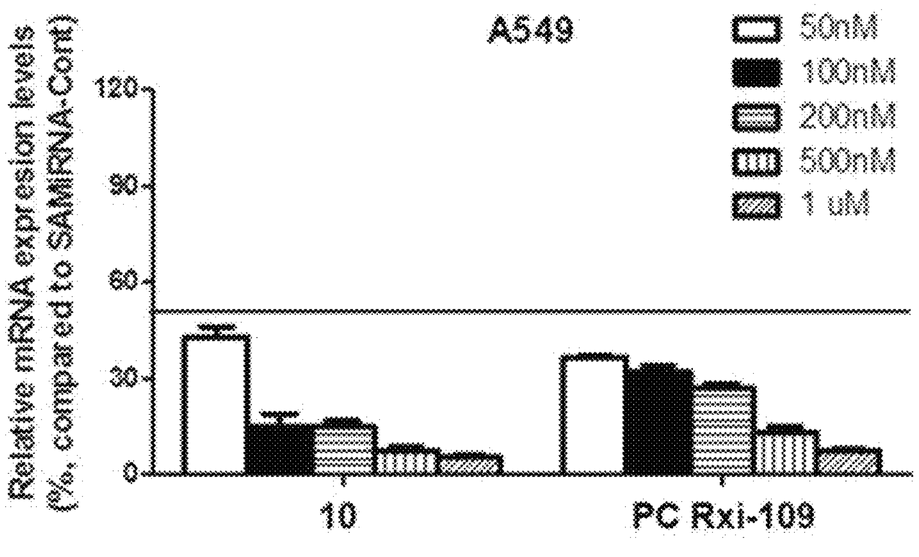
FIG. 4 is a graph showing the results of quantitative analysis of the mRNA expression level of CTGF in Example 4, in which the $IC_{50}$ value of SAMiRNA was determined by analyzing the relative mRNA expression level (%) of CTGF after treatment with SAMiRNA having, as a sense strand, each of the sequence of SEQ ID NO: 10 of the present invention and the sequence of Rxi-109.

Consequently, it was confirmed that all of the CTGF-specific SAMiRNAs having the sequence of SEQ ID NO: 10 as the sense strand reduced the mRNA expression level of CTGF by 50% or more even at a low concentration of 50 nM, thereby inhibiting the CTGF expression with very high efficiency. As shown in FIG. 4, $IC_{50}$ was determined to be 30.75 nM for the CTGF-specific SAMiRNA having the sequence of SEQ ID NO: 10 as the sense strand, indicating that CTGF gene expression was inhibited most effectively, and a superior inhibitory effect was also confirmed when compared to Rxi-109 $IC_{50}$.

TABLE 5

Primer sequence information for qPCR

| Primer | Sequence | SEQ ID NO: |
|---|---|---|
| hGAPDH-F | GGTGAAGGTCGGAGTCAACG | 42 |
| hGAPDH-R | ACCATGTAGTTGAGGTCAATGAAGG | 43 |
| hCTGF-F | CACCAGCATGAAGACATACCG | 44 |
| hCTGF-R | CGTCAGGGCACTTGAACTC | 45 |

(F stands for forward primer and R stands for reverse primer)

TABLE 6

SAMiRNA sequence effectively inhibiting CTGF expression

| SEQ ID NO: | Code Name | Position | Sense strand sequence |
|---|---|---|---|
| 10 | SAMi-CTGF#1330 | 1330-1348 | TGATTTCAGTAGCACAAGT |

Example 5. Comparative Analysis of Inhibition of Human CTGF Expression by DNA/RNA Hybrid and RNA/RNA Hybrid SAMiRNA Including Selected Sequence of SEQ ID NO: 10 as Sense Strand A lung cancer cell line A549 was treated using a double-stranded oligo DNA/RNA hybrid and RNA/RNA hybrid including CTGF-specific SAMiRNA having the sequence of SEQ ID NO: 10 selected in Example 4 as a sense strand, and the relative mRNA expression level (%) of CTGF in the cell line was analyzed.

5.1 Intracellular Processing of SAMiRNA Nanoparticles

A549, which is a human-derived lung cancer cell line, was used to discover SAMiRNA that inhibits CTGF expression, and the A549 cell line was cultured at 37° C. and 5% $CO_2$ in a Gibco™F-12K (Kaighn's) medium (Thermo, US) containing 10% fetal bovine serum (Hyclone, US) and 1% penicillin-streptomycin (Hyclone, US). Using the same medium as above, the A549 cell line was dispensed at a density of $8\times10^4$ cells/well in a 12-well plate (Costar, US), and the next day, SAMiRNA homogenized with deionized distilled water in Example 3.1 was diluted to 200 nM or 600 nM with 1×DPBS and added to the cells. Cell treatment with SAMiRNA was performed a total of 4 times, once every 12 hours, and culture was carried out at 37° C. and 5% $CO_2$.

5.2 SAMiRNA Screening Through Analysis of Human CTGF mRNA Expression Inhibitory Efficacy Total RNA was extracted from the cell line treated with SAMiRNA in Example 5-1 and was synthesized into cDNA, after which the relative mRNA expression level of the CTGF gene was quantified using real-time PCR.

5-2-1 RNA Isolation from SAMiRNA-Treated Cells and cDNA Synthesis

Total RNA was extracted from the cell line treated with SAMiRNA in Example 5-1 using an RNA extraction kit (AccuPrep Cell total RNA extraction kit, Bioneer, Korea), and the extracted RNA was synthesized into cDNA in the following manner using RNA reverse transcriptase (AccuPower® RocketScript™ oligo (dT)20, Bioneer, Korea). Specifically, 1 μg of the extracted RNA was added to AccuPower® RocketScript™ (Korea) contained in each of 0.25 ml Eppendorf tubes, and DEPC (diethyl pyrocarbonate)-treated distilled water was added thereto to achieve a total volume of 20 μl. In a gene amplification system (MyGenie™ Gradient Thermal Block, Bioneer, Korea), two processes of hybridizing RNA with primers at 37° C. for 30 seconds and synthesizing cDNA at 48° C. for 4 minutes were repeated 12 times, after which the amplification reaction was terminated by deactivating the enzyme at 95° C. for 5 minutes.

5-2-2 Relative Quantitative Analysis of Human CTGF mRNA

The relative mRNA expression level of CTGF compared to the SAMiRNA control sample was analyzed in the following manner through SYBR green real-time qPCR using the cDNA synthesized in Example 5-2-1 as a template. Specifically, the cDNA synthesized in Example 5-2-1 was diluted 5-fold with distilled water, and for analysis of the mRNA expression level of CTGF, 3 μl of the diluted cDNA, 25 μl of AccuPower® (Korea), 19 μl of distilled water, and 3 μl of CTGF qPCR primers (SEQ ID NOs: 44 and 45 (Table 5); 10 pmol/μl, respectively, Bioneer, Korea) were added to each well of a 96-well plate to obtain a mixed solution. Meanwhile, in order to normalize the mRNA expression level of CTGF, GAPDH (glyceraldehyde-3-phosphate dehydrogenase), which is a housekeeping (HK) gene, was used as a standard gene. The 96-well plate containing the mixed solution was subjected to the following reaction using an Exicycler™ Quantitative Thermal Block (Bioneer, Korea): reaction at 95° C. for 15 minutes to activate the enzyme and remove the secondary structure of cDNA, 42 cycles each including four processes of denaturation at 94° C. for 30 seconds, annealing at 58° C. for 30 seconds, extension at 72° C. for 30 seconds, and SYBR green scan, and final extension at 72° C. for 3 minutes, after which the temperature was maintained at 55° C. for 1 minute and the melting curve from 55° C. to 95° C. was analyzed.

After termination of PCR, the Ct (threshold cycle) value of each target gene was corrected using the GAPDH gene, and then the difference L in values was calculated using a control group treated with SAMiRNA (SAMiCONT), which is a control sequence that does not induce gene expression inhibition. The relative expression level of the target gene in the cells treated with CTGF-specific SAMiRNA was quantified using the A value and equation 2 (−Δx100).

In order to select highly efficient SAMiRNA among double-stranded oligo DNA/RNA hybrid and RNA/RNA hybrid, SAMiRNA, which is a DNA/RNA hybrid having, as the sense strand, the sequence having the highest efficiency of reduction of the mRNA expression level of CTGF at a final concentration of 200 nM or 600 nM compared to the control group, namely the DNA sequence of SEQ ID NO: 10, was finally selected.

Figure 5:
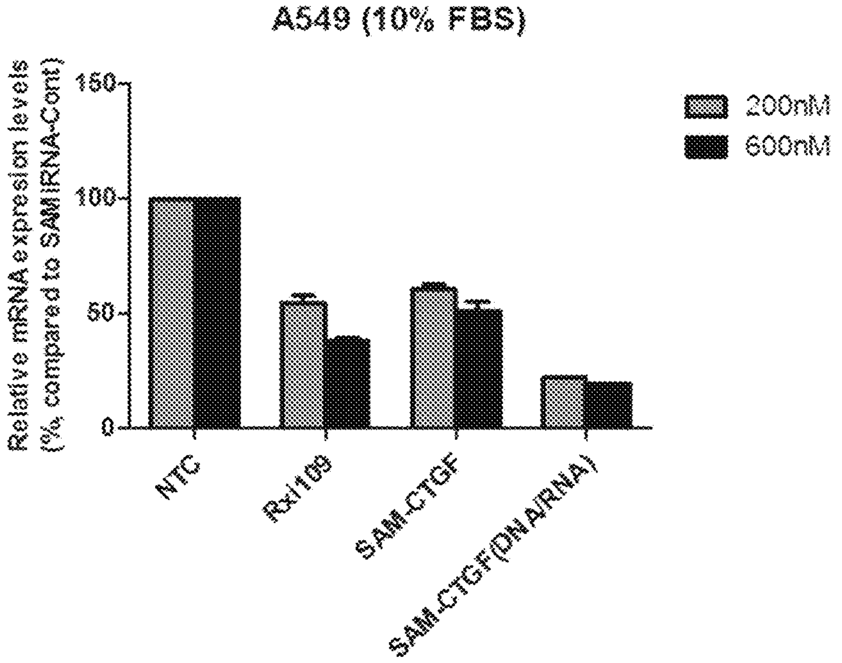
FIG. 5 is a graph showing the results of quantitative analysis of the mRNA expression level of CTGF in Example 5, in which the relative mRNA expression level (%) of CTGF was analyzed using the double-stranded oligo DNA/RNA hybrid and RNA/RNA hybrid including the selected CTGF-specific SAMiRNA, and the relative mRNA expression level (%) of CTGF was determined after treatment of the lung cancer cell line A549 with SAMiRNA having, as a sense strand, the sequence of SEQ ID NO: 10 of the present invention at different concentrations (200 nM and 600 nM)

As shown in FIG. 5, DNA/RNA hybrid SAMiRNA #10, which inhibits CTGF gene expression most effectively, was finally selected from among the double-stranded oligo DNA/RNA hybrid and RNA/RNA hybrid including the selected CTGF-specific SAMiRNA.

Example 6. Screening of SAMiRNA Nanoparticles Inducing RNAi Targeting Rat CTGF

In siRNA therapeutic agents, it is difficult to discover the optimal sequence that may be commonly applied to different strains. Here, US FDA guidelines are provided to verify pharmacological efficacy due to inhibition of expression of the corresponding gene and toxicity due to inhibition of expression of the corresponding gene by designing an siRNA sequence (surrogate sequence; mouse gene-specific siRNA) specific to an animal model (confirmed through an in-vivo efficacy test) that analyzes the therapeutic effect (presentation by Robert T. Dorsam Ph.D. Pharmacology/Toxicology Reviewer, FDA/CDER).

The SAMiRNA-based sequence was discovered using a conventional algorithm-based siRNA design program (Turbo-si-designer owned by the applicant). A total of 94 candidate siRNA sequences were generated from rat CTGF gene (NM_022266.2) full transcript sequences, and the corresponding SAMiRNA was synthesized, after which the rat liver-cancer-derived H4-II-E cell line was treated therewith at 500 nM under cell culture conditions containing 10% FBS, so the in-vitro expression inhibitory effect was primarily screened using the primers shown in Table 8 below (primer sequence information for qPCR) (FIG. 6).

In order to select highly efficient SAMiRNA, secondary screening for the sequences having the highest efficiency of reduction of the mRNA expression level of rat CTGF at a final concentration of 500 nM compared to the control group, namely 12 sequences having reduction efficiency>60% or more (a total of 94 types of SAMiRNA-rat CTGF), was performed at 200 nM and 500 nM in an H4-II-E cell line, which is a rat liver cancer cell line. Consequently, three SAMiRNAs having the sequences of SEQ ID NOs: 46, 47, and 48 as respective sense strands were selected.

Figure 6:
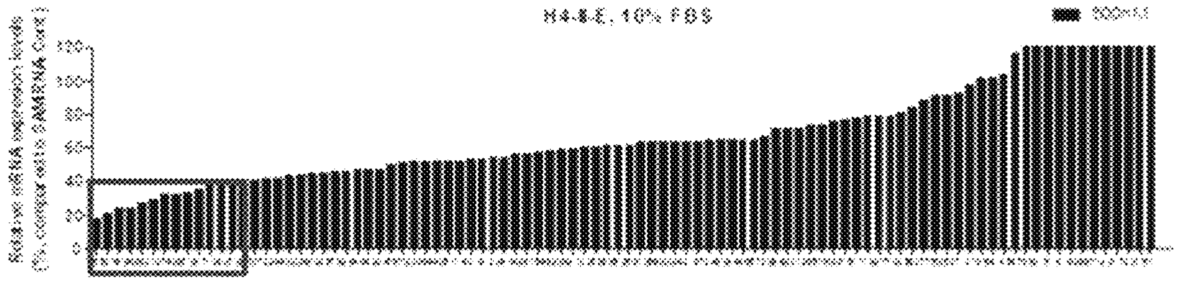
FIG. 6 shows the results of screening of 94 SAMiRNAs targeting rat CTGF and the effects of 12 candidate sequences selected therefrom.
Figure 7:
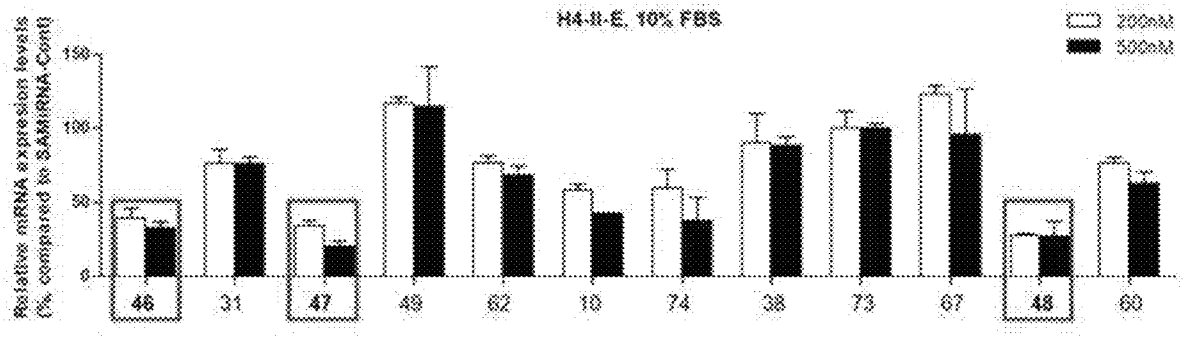
FIG. 7 is a graph showing the results of quantitative analysis of the mRNA expression level of rat CTGF in Example 6, in which the relative mRNA expression level (%) of rat CTGF was determined after treatment of a rat liver cancer cell line H4-II-E with SAMiRNA having, as a sense strand, each of 12 selected candidate sequences including the sequences of SEQ ID NOs: 46, 47, and 48 of the present invention at different concentrations (200 nM and 500 nM)

As shown in FIG. 6, three SAMiRNAs, which inhibit rat CTGF gene expression most effectively, were finally selected from among 94 SAMiRNAs targeting rat CTGF (FIG. 8), and the sequence information of the corresponding SAMiRNA is shown in Table 9 below.

In order to select highly efficient SAMiRNA, SAMiRNA-rat CTGF #46, having, as the sense strand, the sequence having the highest efficiency of reduction of the mRNA expression level of rat CTGF at a final concentration of 25, 50, 100, 200, 400, or 800 nM compared to the control group, namely the sequence of SEQ ID NO: 46, was finally selected.

Figure 8:
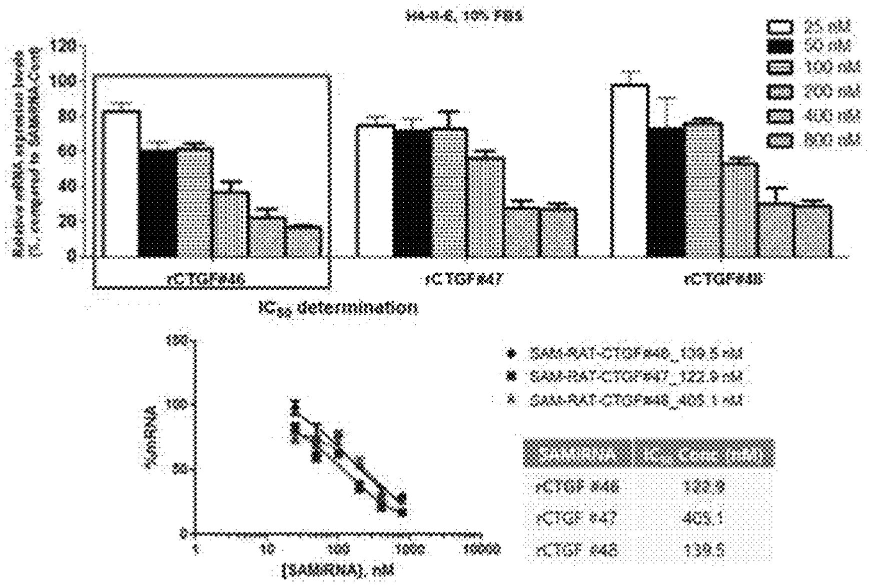
FIG. 8 is graphs showing the results of quantitative analysis of the mRNA expression level of rat CTGF in Example 6, in which the $IC_{50}$ value of SAMiRNA was determined by analyzing the relative mRNA expression level (%) of rat CTGF after treatment of the rat liver cancer cell line H4-II-E with SAMiRNA having, as a sense strand, each of the sequences of SEQ ID NOs: 46, 47, and 48 of the present invention at different concentrations (25, 50, 100, 200, 400, and 800 nM)

As shown in FIG. 8, $IC_{50}$ was determined to be 122.9 nM for rat-CTGF-specific SAMiRNA having the sequence of SEQ ID NO: 46 as the sense strand, indicating that rat CTGF gene expression was most effectively inhibited.

Figure 9:
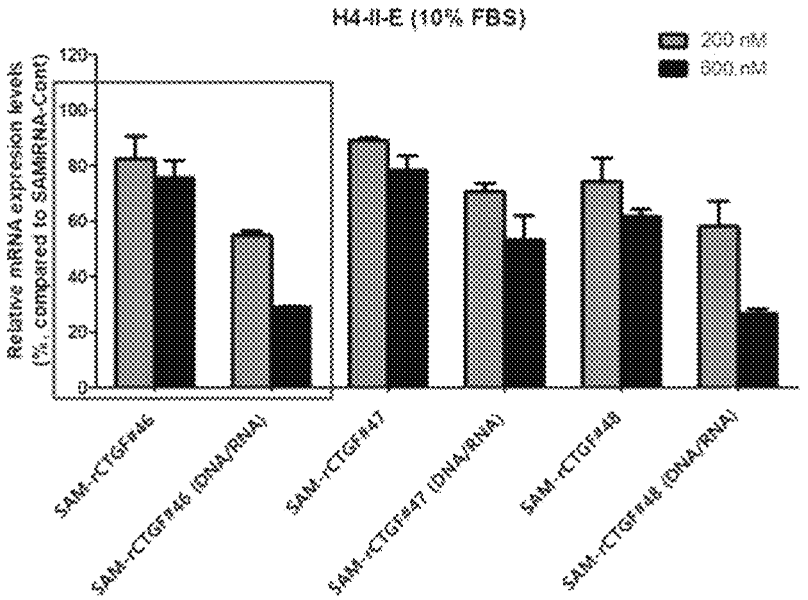
FIG. 9 is a graph showing the results of quantitative analysis of the mRNA expression level of rat CTGF in Example 6, in which the relative mRNA expression level (%) of rat CTGF was analyzed using the double-stranded oligo DNA/RNA hybrid and RNA/RNA hybrid including the selected rat-CTGF-specific SAMiRNA, and the relative mRNA expression level (%) of rat CTGF was determined after treatment of the liver cancer cell line H4-II-E with SAMiRNA having, as a sense strand, each of the sequences of SEQ ID NOs: 46, 47, and 48 of the present invention at different concentrations (200 nM and 600 nM)

In addition, as shown in FIG. 9, DNA/RNA hybrid SAMiRNA #46, which inhibits rat CTGF gene expression most effectively, was finally selected from among the double-stranded oligo DNA/RNA hybrid and RNA/RNA hybrid including the selected rat-CTGF-specific SAMiRNA.

TABLE 8

(F stands for forward primer and R stands for reverse primer)

| Primer | Sequence |
|---|---|
| rat-GAPDH-F | AACATCATCCCTGCATCCAC (SEQ ID NO: 49) |
| rat-GAPDH-R | CGGATACATTGGGGGTAGGA (SEQ ID NO: 50) |
| rat-CTGF-F | CAAGGGTCTCTTCTGCGAC (SEQ ID NO: 51) |
| rat-CTGF-R | ATTTGCAACTGCTTTGGAAGG (SEQ ID NO: 52) |

TABLE 9

| SEQ ID NO: | Code Name | Position | Sense strand sequence |
|---|---|---|---|
| 46 | SAMi-rCTGF#46 | 195-213 | GACACTGGTTTCGAGACAG |
| 47 | SAMi-rCTGF#47 | 182-200 | CCTGTCAATCTCAGACACT |
| 48 | SAMi-rCTGF#48 | 984-1002 | CATCCGGACGCCTAAAATT |

Example 7. Verification of Efficacy of SAMiRNA-Rat CTGF Through Intradermal Administration in Wound-Induced Keloid Animal Model The efficacy of SAMi-rCTGF on wounds induced with an 8 mm biopsy punch (Biopsy punch, BP-80F, Kai, Japan) was analyzed. For the experiment, 7-week-old rats were purchased (SD Rats, Nara Biotech, Gangnam, Korea) and acclimatized for 1 week. Wounds were made on the back skin of the rats using an 8 mm biopsy punch. 1200 μg/site of each of saline (PBS) for a negative control group, SAMiRNA-rCTGF #46 DNA/RNA(D/R) for an experimental group, and SAMiRNA-rCTGF #46 RNA/RNA(R/R) for another experimental group was intradermally administered thereto a total of two times 2 days before wound induction and on the day of wound induction. The rats were sacrificed on the 3rd day after wound induction.

7-1. Analysis of Gene Expression for SAMiRNA in Wound-Induced Keloid Animal Model The rat skin tissue treated with SAMiRNA was obtained and primarily ground using a mortar and pestle and liquid nitrogen. The ground tissue was placed in a lysis buffer of an RNA extraction kit (AccuPrep Cell total RNA extraction kit, Bioneer, Korea) and secondarily ground using a homogenizer. Thereafter, total RNA was extracted according to the manufacturer's protocol. The extracted RNA was synthesized into cDNA using RNA reverse transcriptase (AccuPower® RocketScript™RT Premix with oligo (dT)20, Bioneer, Korea) in the following manner.

TABLE 10

| RT parameter | | |
|---|---|---|
| Step | Temperature | Time |
| 1 | 37° C. | 30 sec |
| 2 | 48° C. | 4 min |
| 3 | 55° C. | 30 sec |
| 4 | Go to step 1 | 12 cycle |
| 5 | 95° C. | 5 min |

The relative expression level of total mRNA in each group was analyzed in the following manner through SYBR green real-time qPCR using the synthesized cDNA as a template. Specifically, the synthesized cDNA was diluted 10-fold with distilled water, and for analysis of the mRNA expression level of CTGF, 10 μl of the diluted cDNA, 25 μl of AccuPower® GreenStar™ (Korea), 20 μl of distilled water, and 5 μl of CTGF qPCR primers (3 pmol/μl each, Table 11) were added to each well of a 96-well plate to obtain a mixed solution. Meanwhile, in order to normalize the mRNA expression levels of CTGF, fibronectin, and Col3α1, RPL13A, which is a housekeeping (HK) gene, was used as a standard gene. After termination of qPCR, the Ct (threshold cycle) value of each target gene was corrected using the RPL13A gene, the ΔCt value of the target gene was determined, and then the ΔΔCt value thereof compared to the control group was calculated. The relative expression levels of CTGF, fibronectin, and Col3α1 genes were quantified using the ΔΔCt value and equation 2 (−ΔΔCt×100).

TABLE 11

(F stands for forward primer and R stands for reverse primer)

| Primer | Sequence |
|---|---|
| Rat Rpl13a F | AGGGGCAGGTTCTAGTATTG (SEQ ID NO: 53) |
| Rat Rpl13a R | GCGTACAACCACCACCTTTC (SEQ ID NO: 54) |
| Rat Ctgf F | AGGAGTGGGTGTGTGATGAG (SEQ ID NO: 55) |
| Rat Ctgf R | TTGGCTCGCATCATAGTTGG (SEQ ID NO: 56) |

TABLE 12

| Step | Temperature | Time |
|---|---|---|
| qPCR parameter | | |
| 1 | 95° C. | 10 min |
| 2 | 95° C. | 5 sec |

TABLE 12-continued

| Step | Temperature | Time |
|---|---|---|
| 3 | 58° C. | 25 sec |
| 4 | 72° C. Scan | 30 sec |
| 5 | Go to step 2 | 40 cycle |

Consequently, it was confirmed that CTGF expression was significantly reduced in the group treated with 1200 μg of SAMiRNA-rCTGF(D/R) compared to the group treated with saline in wound-induced rats, and a statistically significant reduction was also confirmed in the group treated with 1200 μg of SAMiRNA-rCTGF(D/R) compared to the group treated with 1200 μg of SAMiRNA-rCTGF(R/R).

Figure 10:
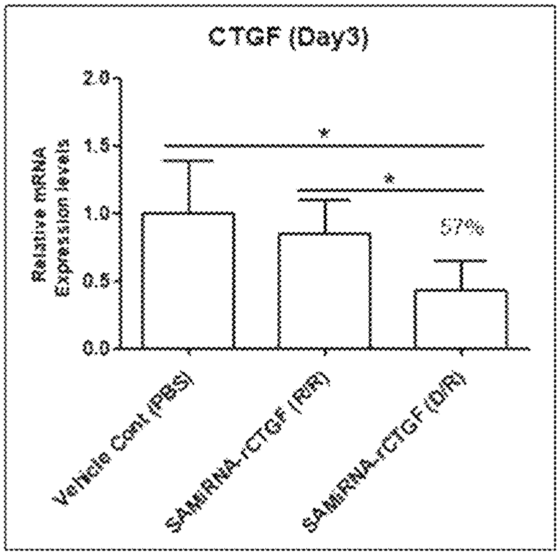
FIG. 10 is a graph showing the results of real-time PCR analysis of skin tissue after intradermal administration of 1200 μg of each of SAMiRNA-rCTGF(D/R) #46 and SAMiRNA-rCTGF(R/R) #46 to wound-induced keloid model mice in Example 7 and the relative mRNA expression level (%) of a target gene CTGF.

As shown in FIG. 10, it was concluded that the double-stranded oligo DNA/RNA hybrid most effectively inhibited CTGF gene expression compared to the RNA/RNA hybrid, among hybrids including the selected rCTGF-specific SAMiRNA.

Although specific embodiments of the present invention have been disclosed in detail above, it will be obvious to those skilled in the art that the description is merely of preferable exemplary embodiments and is not to be construed as limiting the scope of the present invention. Therefore, the substantial scope of the present invention will be defined by the appended claims and equivalents thereof.

INDUSTRIAL APPLICABILITY

According to the present invention, a double-stranded oligonucleotide construct including a CTGF-specific double-stranded oligonucleotide and a pharmaceutical composition containing the same as an active ingredient are capable of inhibiting the expression of CTGF with high efficiency without side effects, and are very effective at preventing and treating diseases and respiratory diseases caused by excessive fibrosis.

SEQUENCE LIST FREE TEXT

An electronic file is attached.

The invention claimed is:

1. A connective growth tissue factor (CTGF)-specific double-stranded oligonucleotide construct for inducing RNAi via siRNA or shRNA, having a structure of Structural Formula (1) below:

A-X—R—Y—B Structural Formula (1)

wherein in Structural Formula 1, A is a hydrophilic material, B is a hydrophobic material, X and Y are each independently a simple covalent bond or a linker-mediated covalent bond, and R is a double-stranded oligonucleotide for inducing RNAi via siRNA or shRNA, said double-stranded oligonucleotide comprising a sense strand consisting of the sequence of SEQ ID NO: 10 and an antisense strand comprising a sequence complementary thereto, wherein the sense strand is DNA, and the antisense strand is RNA.

2. The CTGF-specific double-stranded oligonucleotide construct according to claim 1, having a structure of Structural Formula (2) below:

Structural Formula (2)

A—X—S—Y—B
AS in Structural Formula (2), S and AS are a sense strand and an antisense strand of the double-stranded oligonucleotide according to claim 1, respectively, and A, B, X, and Y are as defined in claim 1.

3. The CTGF-specific double-stranded oligonucleotide construct according to claim 2, having a structure of Structural Formula (3) or Structural Formula (4) below:

Sturctural Formula (3)

A—X—5′ S 3′—Y—B
AS

Structural Formula (4)

A—X—3′ S 5′—Y—B
AS in Structural Formulas (3) and (4), A, B, X, Y, S, and AS are as defined in claim 2, and 5' and 3' are 5' and 3' ends of the sense strand of the double-stranded oligonucleotide.

4. The CTGF-specific double-stranded oligonucleotide construct according to claim 1, wherein the hydrophilic material has a structure of Structural Formula (5) or Structural Formula (6) below:

$(A'_m\text{-}J)_n$ Structural Formula (5)

$(J\text{-}A'_m)_n$ Structural Formula (6)

in Structural Formula (5) or Structural Formula (6), A' is a hydrophilic material monomer, J is a linker connecting m hydrophilic material monomers to each other or connecting m hydrophilic material monomers and a double-stranded oligonucleotide to each other, m is an integer of 1 to 15, n is an integer of 1 to 10, the hydrophilic material monomer A' is any one compound selected from among compounds (1) to (3) below, and the linker (J) is selected from the group consisting of $—PO_3—$, $—SO_3—$, and $—CO_2—$:

Compound (1)

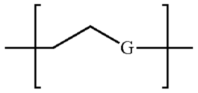

in compound (1), G is selected from the group consisting of O, S, and NH;

Compound (2)

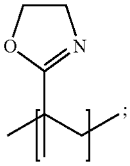

; and

Compound (3)

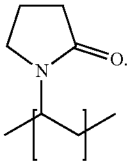

5. The CTGF-specific double-stranded oligonucleotide construct according to claim 4, having a structure of Structural Formula (7) or Structural Formula (8) below:

$(A'_m\text{-}J)_n$-X—R—Y—B Structural Formula (7)

$(J\text{-}A'_m)_n$—X—R—Y—B. Structural Formula (8)

6. Nanoparticles comprising the double-stranded oligonucleotide construct according to claim 1.

7. The nanoparticles according to claim 6, wherein the nanoparticles are configured such that double-stranded oligonucleotide constructs comprising double-stranded oligonucleotides comprising different sequences are mixed.

8. A method of treating fibrosis or a respiratory disease by inhibiting expression of CTGF, in a subject in need thereof, comprising administering to the subject a pharmaceutical composition comprising the CTGF-specific double-stranded oligonucleotide construct according to claim 1.

9. A method of preventing or treating fibrosis or a respiratory disease by inhibiting expression of CTGF, in a subject in need thereof, comprising administering to the subject the nanoparticles according to claim 6 as an active ingredient.

10. The method according to claim 8, wherein the respiratory disease is any one selected from the group consisting of chronic obstructive pulmonary disease (COPD), asthma, acute or chronic bronchitis, allergic rhinitis, productive cough, bronchitis, bronchiolitis, laryngopharyngitis, tonsillitis, and laryngitis.

11. The method according to claim 8, wherein the fibrosis is any one selected from the group consisting of idiopathic pulmonary fibrosis (IPF), liver fibrosis, cirrhosis, myelofibrosis, myocardial fibrosis, renal fibrosis, keloid, pulmonary fibrosis, cardiac fibrosis, and radiation-induced fibrosis.

12. The method according to claim 9, wherein the respiratory disease is any one selected from the group consisting of chronic obstructive pulmonary disease (COPD), asthma, acute and chronic bronchitis, allergic rhinitis, productive cough, bronchitis, bronchiolitis, laryngopharyngitis, tonsillitis, and laryngitis.

13. The method according to claim 9, wherein the fibrosis is any one selected from the group consisting of idiopathic pulmonary fibrosis (IPF), liver fibrosis, cirrhosis, myelofibrosis, myocardial fibrosis, renal fibrosis, keloid, pulmonary fibrosis, cardiac fibrosis, and radiation-induced fibrosis.

14. A method of treating fibrosis or a respiratory disease by inhibiting expression of CTGF, in a subject in need thereof, comprising administering to the subject the CTGF-specific double-stranded oligonucleotide construct according to claim 1 as an active ingredient.

15. The method according to claim 14, wherein the respiratory disease is any one selected from the group consisting of chronic obstructive pulmonary disease (COPD), asthma, acute and chronic bronchitis, allergic rhinitis, productive cough, bronchitis, bronchiolitis, laryngopharyngitis, tonsillitis, and laryngitis.

16. The method according to claim 14, wherein the fibrosis is any one selected from the group consisting of idiopathic pulmonary fibrosis (IPF), liver fibrosis, cirrhosis, myelofibrosis, myocardial fibrosis, renal fibrosis, keloid, pulmonary fibrosis, cardiac fibrosis, and radiation-induced fibrosis.

* * * * *

```
SEQUENCE LISTING

<160> NUMBER OF SEQ ID NOS: 60

<210> SEQ ID NO 1
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 1

atgtacagtt atctaagtt                                                   19


<210> SEQ ID NO 2
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 2

tgtacagtta tctaagtta                                                   19


<210> SEQ ID NO 3
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 3

gtacagttat ctaagttaa                                                   19


<210> SEQ ID NO 4
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 4

atggaaattc tgctcagat                                                   19
```

-continued

<210> SEQ ID NO 5
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 5
tggaaattct gctcagata 19

<210> SEQ ID NO 6
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 6
ggaaattctg ctcagatag 19

<210> SEQ ID NO 7
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 7
atttcagtag cacaagtta 19

<210> SEQ ID NO 8
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 8
tttcagtagc acaagttat 19

<210> SEQ ID NO 9
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 9
ttcagtagca caagttatt 19

<210> SEQ ID NO 10
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 10
tgatttcagt agcacaagt 19

<210> SEQ ID NO 11
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

-continued

<400> SEQUENCE: 11
gatttcagta gcacaagtt 19

<210> SEQ ID NO 12
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 12
taaaaatgat ttcagtagc 19

<210> SEQ ID NO 13
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 13
aaaaatgatt tcagtagca 19

<210> SEQ ID NO 14
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 14
aaaatgattt cagtagcac 19

<210> SEQ ID NO 15
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 15
tcagtagcac aagttattt 19

<210> SEQ ID NO 16
<211> LENGTH: 19
<212> TYPE: DNA
<213> ORGANISM: Artificial Sequence
<220> FEATURE:
<223> OTHER INFORMATION: CTGF Specific SAMiRNA Candidate (Sense)

<400> SEQUENCE: 16
cagtagcaca agttattta 19

<210> SEQ ID NO 17
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 17
aacuuagaua acuguacau 19

<210> SEQ ID NO 18
<211> LENGTH: 19

-continued

<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 18
uaacuuagau aacuguaca 19

<210> SEQ ID NO 19
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 19
uuaacuuaga uaacuguac 19

<210> SEQ ID NO 20
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 20
aucugagcag aauuuccau 19

<210> SEQ ID NO 21
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 21
uaucugagca gaauuucca 19

<210> SEQ ID NO 22
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 22
cuaucugagc agaauuucc 19

<210> SEQ ID NO 23
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 23
uaacuugugc uacugaaau 19

<210> SEQ ID NO 24
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 24
auaacuugug cuacugaaa 19

<210> SEQ ID NO 25
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 25
aauaacuugu gcuacugaa 19

<210> SEQ ID NO 26
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 26
acuugugcua cugaaauca 19

<210> SEQ ID NO 27
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 27
aacuugugcu acugaaauc 19

<210> SEQ ID NO 28
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 28
gcuacugaaa ucauuuuua 19

<210> SEQ ID NO 29
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 29
ugcuacugaa aucauuuuu 19

<210> SEQ ID NO 30
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 30
gugcuacuga aaucauuuu 19

<210> SEQ ID NO 31
<211> LENGTH: 19
<212> TYPE: RNA
<213> ORGANISM: Artificial Sequence -continued
<220> FEATURE:
<223> OTHER INFORMATION: CTGF Specific SAMiRNA Candidate (Antisense)

<400> SEQUENCE: 31
aaauaacuug ugcuacuga 19

<210> SEQ ID NO 32
<211> LENGTH: 19
<212> TYPE: RNA
<213> ORGANISM: Artificial Sequence
<220> FEATURE:
<223> OTHER INFORMATION: CTGF Specific SAMiRNA Candidate (Antisense)

<400> SEQUENCE: 32
uaaauaacuu gugcuacug 19

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
caccagcatg aagacatacc g 21

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
cgtcagggca cttgaactc 19

<210> SEQ ID NO 35
<211> LENGTH: 23
<212> TYPE: DNA
<213> ORGANISM: Artificial Sequence
<220> FEATURE:
<223> OTHER INFORMATION: Probe

<400> SEQUENCE: 35
ccgacggccg atgctgcacc ccc 23

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gtgtttgacg gcatcccacc 20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
taggcttcag acgcacgacc 20

<210> SEQ ID NO 38
<211> LENGTH: 21
<212> TYPE: DNA
<213> ORGANISM: Artificial Sequence
<220> FEATURE:
<223> OTHER INFORMATION: Probe

<400> SEQUENCE: 38
aagcggatgg tggttcctgc t 21

<210> SEQ ID NO 39
<211> LENGTH: 19
<212> TYPE: DNA
<213> ORGANISM: Artificial Sequence
<220> FEATURE:
<223> OTHER INFORMATION: Primer

<400> SEQUENCE: 39
caccacagct cttccactc 19

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
atcccagaac tctccgaagc 20

<210> SEQ ID NO 41
<211> LENGTH: 20
<212> TYPE: DNA
<213> ORGANISM: Artificial Sequence
<220> FEATURE:
<223> OTHER INFORMATION: Probe

<400> SEQUENCE: 41
acccttgccg ggcaccactc 20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
ggtgaaggtc ggagtcaacg 20

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
accatgtagt tgaggtcaat gaagg 25

<210> SEQ ID NO 44
<211> LENGTH: 21
<212> TYPE: DNA
<213> ORGANISM: Artificial Sequence
<220> FEATURE:
<223> OTHER INFORMATION: Primer -continued

<400> SEQUENCE: 44
caccagcatg aagacatacc g 21

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
cgtcagggca cttgaactc 19

<210> SEQ ID NO 46
<211> LENGTH: 19
<212> TYPE: DNA
<213> ORGANISM: Artificial Sequence
<220> FEATURE:
<223> OTHER INFORMATION: SAMi-rCTGF Sense

<400> SEQUENCE: 46
gacactggtt tcgagacag 19

<210> SEQ ID NO 47
<211> LENGTH: 19
<212> TYPE: DNA
<213> ORGANISM: Artificial Sequence
<220> FEATURE:
<223> OTHER INFORMATION: SAMi-rCTGF Sense

<400> SEQUENCE: 47
cctgtcaatc tcagacact 19

<210> SEQ ID NO 48
<211> LENGTH: 19
<212> TYPE: DNA
<213> ORGANISM: Artificial Sequence
<220> FEATURE:
<223> OTHER INFORMATION: SAMi-rCTGF Sense

<400> SEQUENCE: 48
catccggacg cctaaaatt 19

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
aacatcatcc ctgcatccac 20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
cggatacatt gggggtagga 20

<210> SEQ ID NO 51

-continued

<211> LENGTH: 19
<212> TYPE: DNA
<213> ORGANISM: Artificial Sequence
<220> FEATURE:
<223> OTHER INFORMATION: Primer

<400> SEQUENCE: 51
caagggtctc ttctgcgac 19

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
atttgcaact gctttggaag g 21

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
aggggcaggt tctagtattg 20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
gcgtacaacc accacctttc 20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
aggagtgggt gtgtgatgag 20

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
ttggctcgca tcatagttgg 20

<210> SEQ ID NO 57
<211> LENGTH: 13
<212> TYPE: RNA
<213> ORGANISM: Artificial Sequence
<220> FEATURE:
<223> OTHER INFORMATION: Rxi-109 Sense

<400> SEQUENCE: 57

-continued

```
gcaccuuucu aga                                                         13


<210> SEQ ID NO 58
<211> LENGTH: 19
<212> TYPE: RNA
<213> ORGANISM: Artificial Sequence
<220> FEATURE:
<223> OTHER INFORMATION: Rxi-109 Antisense

<400> SEQUENCE: 58

ucuagaaagg ugcaaacau                                                   19


<210> SEQ ID NO 59
<211> LENGTH: 19
<212> TYPE: RNA
<213> ORGANISM: Artificial Sequence
<220> FEATURE:
<223> OTHER INFORMATION: SAMiRNA(SAMiCONT) Sense

<400> SEQUENCE: 59

cuuacgcuga guacuucga                                                   19


<210> SEQ ID NO 60
<211> LENGTH: 19
<212> TYPE: RNA
<213> ORGANISM: Artificial Sequence
<220> FEATURE:
<223> OTHER INFORMATION: SAMiRNA(SAMiCONT) Antisense

<400> SEQUENCE: 60

ucgaaguacu cagcguaag                                                   19
```